US007378513B2

(12) United States Patent
Ooi et al.

(10) Patent No.: US 7,378,513 B2
(45) Date of Patent: May 27, 2008

(54) ISOLATED PROTEINS FROM A TRADITIONAL CHINESE MEDICINE YUZHU AND USE THEREOF

(75) Inventors: Linda Shiou Mei Ooi, Hong Kong (CN); Samuel Sai Ming Sun, Honolulu, HI (US); Vincent Eng Choon Ooi, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 234 days.

(21) Appl. No.: 11/189,342

(22) Filed: Jul. 26, 2005

(65) Prior Publication Data

US 2007/0027078 A1     Feb. 1, 2007

(51) Int. Cl.
*C07H 21/00*     (2006.01)
*C12N 5/04*      (2006.01)

(52) U.S. Cl. .................... 536/23.6; 435/69.1; 435/419; 435/468

(58) Field of Classification Search ............... 536/23.1, 536/23.6
See application file for complete search history.

(56) References Cited

FOREIGN PATENT DOCUMENTS

| CN | 1537943 | 10/2004 |
|---|---|---|
| CN | 1557842 | 12/2004 |
| CN | 1562350 | 1/2005 |

OTHER PUBLICATIONS

Appendix A—Sequence alignment of SEQ ID No. 1 and van Damme U44775 from Plant Mol. Biol. 1996 reference, no date.*
Bowie et al., Deciphering the Message in Protein Sequences: Tolerance to Amino Acid Substitutions. Science. 1990. vol. 247, pp. 1306-1310.*
Wells, J.A., Additivity of Mutational Effects in Proteins. Biochemistry. 1990, vol. 29, No. 37, pp. 8509-8517.*
Appendix B—Sequence alignment of SEQ ID No. 1 and Bao et al. from AF521656, no date.*
GenBank accession No. AF521656, Jul. 14, 2002, Bao, J. et al. "Gene cloing of *Polygongtum crytronema* Hua lectin II".
GenBank accession No. U44775, Sep. 4, 1996, Van Damme, E. J. et al., "Molecular cloning of the lectin and a lectin-related protein from common Solomon's seal".
Koike, T., Titioni, K., Suzuki, M., Beppu, H., Kuzuya, H., Maruta, K., Shimp, K., and Fujita, K. 1995. The complete amino acid sequence of a mannose-binding lectinf from "Kidachi aloe" (aloe *arborescens* var. *natalensis* Berger). *Biochemical and Biophysical Research Communication*, 214: 163-170.
Ooi, L.S. M 1998 Isolation, characterization and cloning of lectins from the Chinese daffodil *Narcissus tazetta* var. *chinesis* Ph. D. thesis, the Chinese University of Hong Kong.
Ooi, L.S.M., Ng, T.B., Geng, Y.Q. and Ooi, V.E.C. 2000b. Lectins from bulbs of Chinese daffodil *Narcissus tazetta* (family Amaryllidaceae). *Biochemistry and Cell Biology*, 78: 463-468.
Ooi, L.S.M., Sun, S.S.M. Ng, T.B. and Ooi, V.E.C. 2001. Molecular cloning and the cDNA-derived amino acid sequence of *Narcisses tazetta* isolectins. *Journal of Protien Chemistry* 20: 305-310.
Ooi, L.S.M., Ng, T.B., Sun, S.S.M., Ooi, V.E.C. 2000a Mannose-Specific Isolectins with Different Hemaggultinating Potencies Isolated from Chinese Daffodil (*Narcissus tazetta* var. *chinesis*) Leaves. *Journal of Protien Chemistry*, 19: 163-167.
Ooi, L.S.M., Wang, H., Ng, T.B. and Ooi, E.C. 1998. Isolation and characterization of a mannose-binding lectin from leaves of the Chinese daffodil *Narcissus tazetta*. *Biochemistry and Cell biology*, 76: 601-608.
Ooi, L.S.M., Yu, H., Chen, C.M., Sun, S.S.M. and Ooi, V.E.C. 2002. Isolation and characterization of a bioactive mannose-binding protein from the Chinese chive *Allium turberosum*. *Journal of Agricultural and Food Chemistry*, 50: 696-700.
Van Damme, E.J.M., Barre, A., Rouge, P., Van Leuven, F., Balzarini, J. and Peumans, W.J. 1996. Molecular cloning of the lectin and a lectin-related protein from common Solomon's seal (*Polygonatum multiflorum*). *Plant Molecular Biology*, 31: 657-672.
Van Damme, E.J.M., Kaku, H., Perini, F., Goldstein, I.J., Peeters, B., Yagi, F., Decock, B., and Peumans, W.J. 1991. Biosynthesis, primary structure and molecular cloning of snowdrop (*Galanthus nivalis* L.) lectin. *European Journal of Biochemistry*, 202: 23-30.
Van Damme, E.J.M., Smeets, K., and Peumans, W.J. 1995. The mannose-binding monocot lectins and their genes. In "*Lectins, Biomedical Perspectives*" Pusztai, A. and Bardocz, S. Eds., p. 67, Taylor & Francis.
Van Damme, E.J.M., Smeets, K., Torrekens, S., Van Leuven, F., Goldstein, I.J., and Peumans, W.J., 1992. The closely related homomeric and heterodimeric mannose-binding lectins from garlic are encoded by one-domain and two-domain lectin genes, respectively. *European Journal of Biochemistry*, 206: 413-420.

* cited by examiner

*Primary Examiner*—Robert B. Mondesi
*Assistant Examiner*—Anand U Desai
(74) *Attorney, Agent, or Firm*—Knobbe, Martens, Olson & Bear LLP

(57) ABSTRACT

Disclosed is an isolated protein from the Chinese medicinal herb, Yuzhu, *Polygonatum odoratum* (Liliaceae). The protein disclosed is an effective agent showing potent antiviral activities while demonstrating antiproliferative effect on HL-60 leukemia and MCF-7 breast cancer cell lines in vitro. A method of obtaining the target protein and use thereof are also provided.

19 Claims, 15 Drawing Sheets

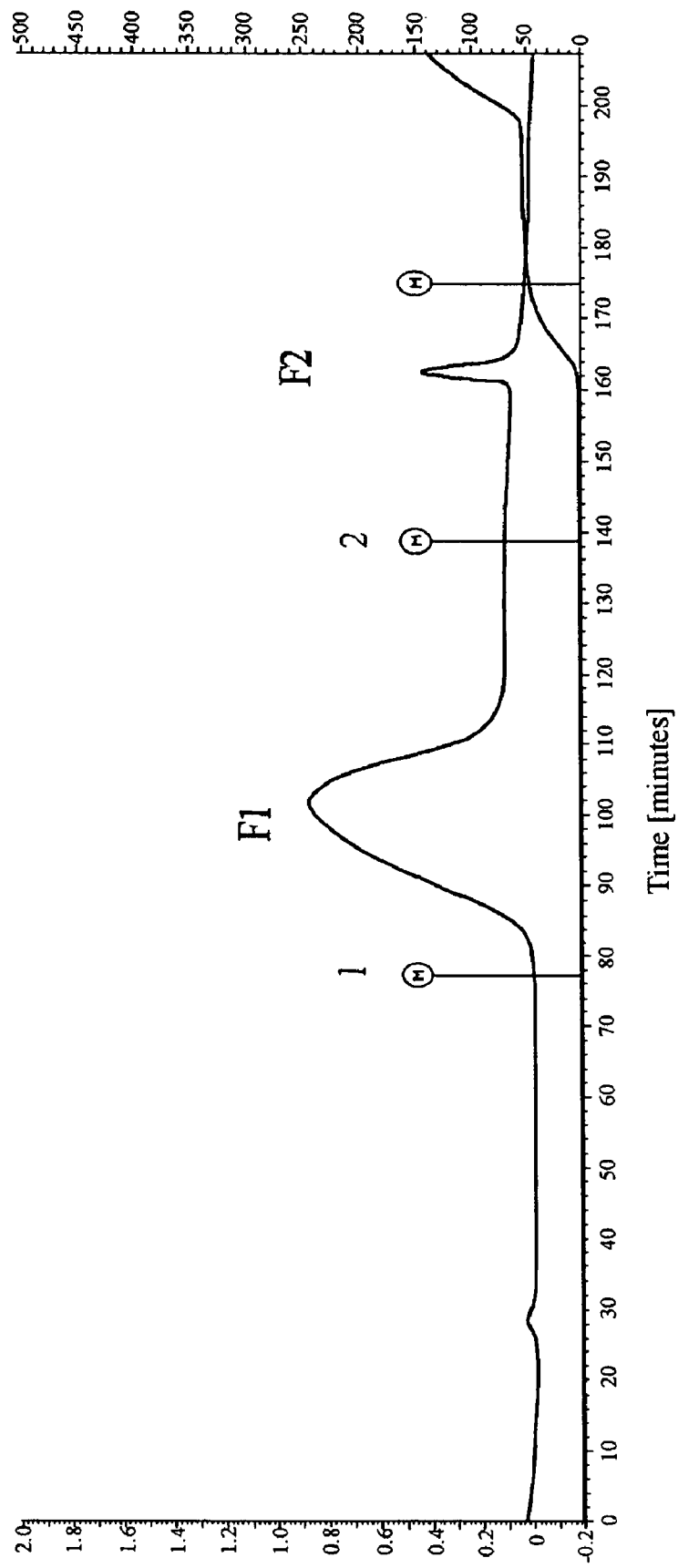
Fig.1a Chromatogran of POL (F2) on a fetuin-agarose column (5x1.5cm) with a flow rate at 0.5ml/min

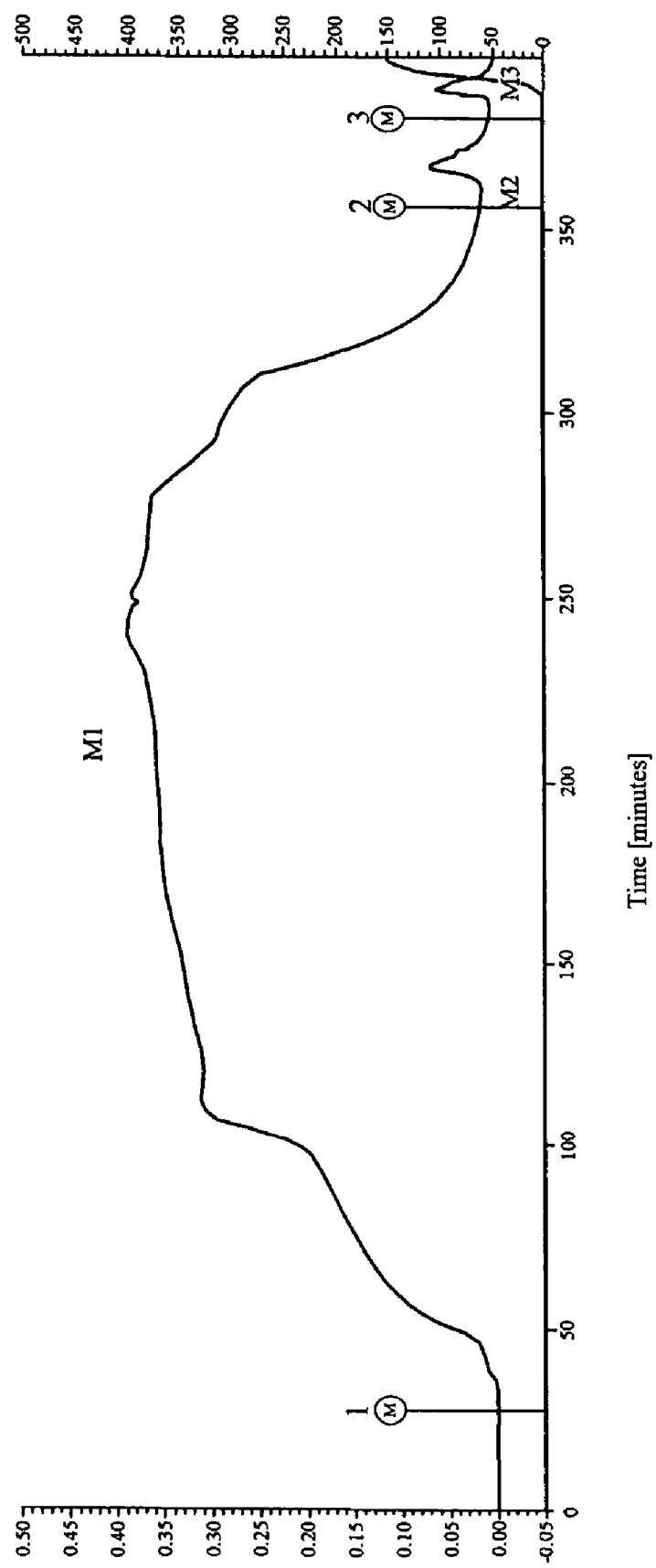
Fig.1b Chromatogram of POL (M2) on a mannose-agarose affinity column (5x1.5cm) with a flow rate at 0.5ml/min

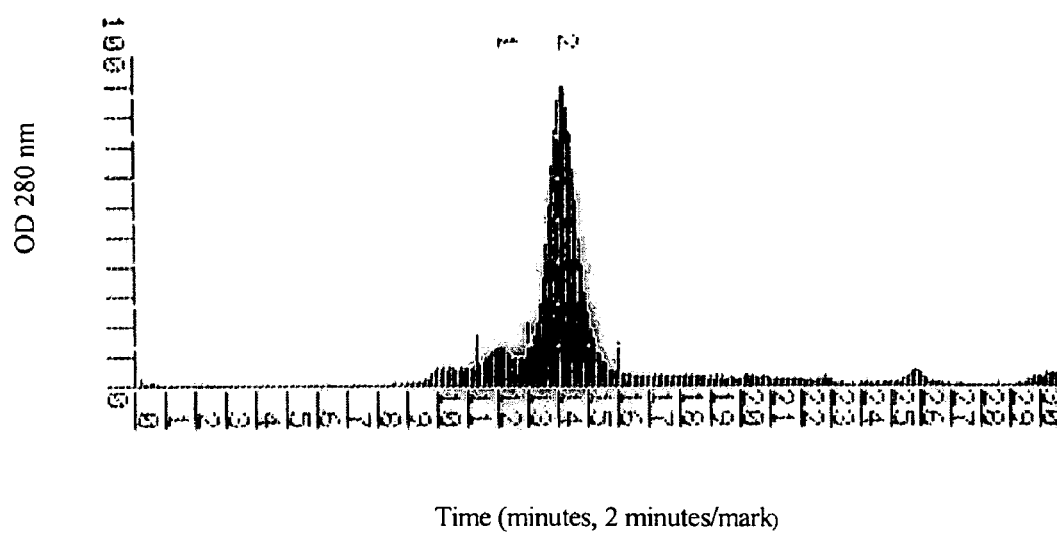
Fig. 2  Chromatogram of POL (peak 2) on Superdex 75 HR10/30 column

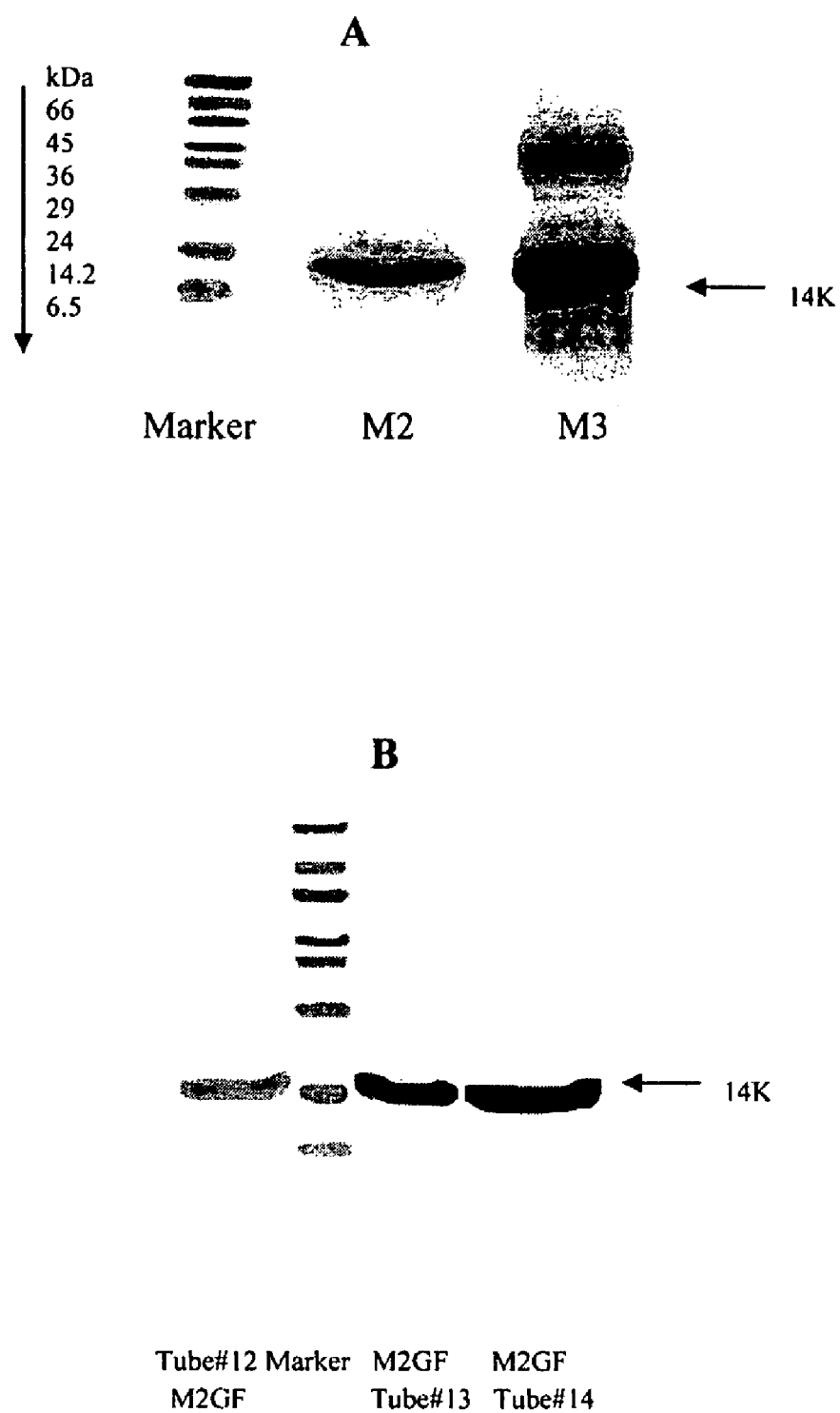
Fig. 3a SDS-PAGE of M2 fraction before and after gel filtration on a Superdex 75 HR 10/30 column

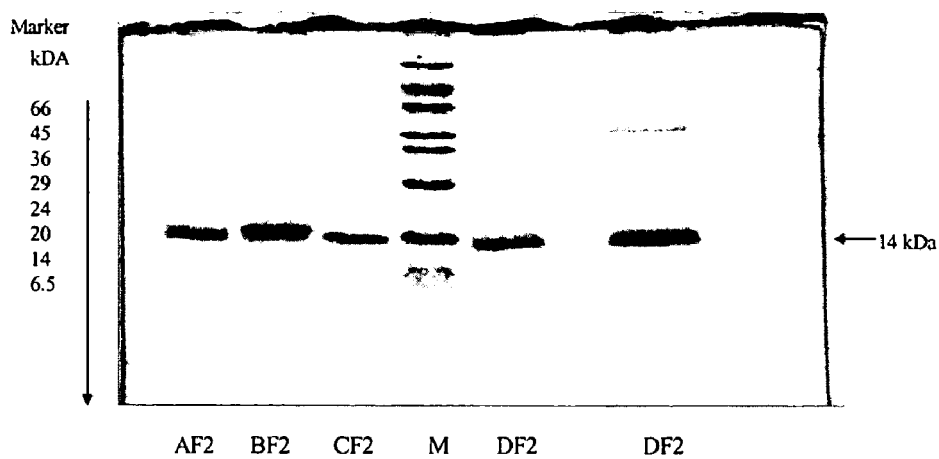
Fig. 3b SDS-PAGE of F2 fractions isolated from various species of *Polygonatum*, Yuzhu
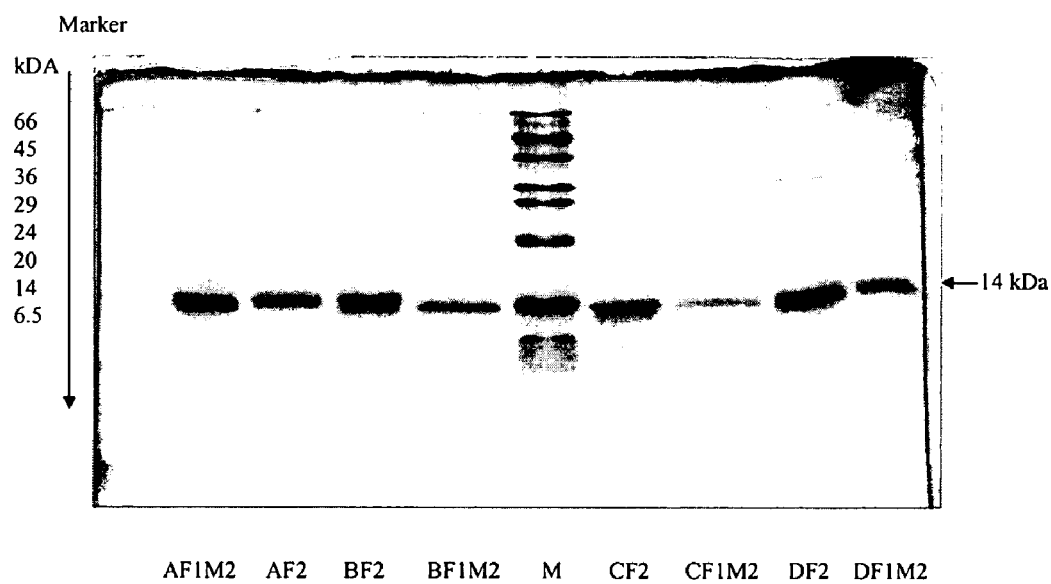
Fig. 3c SDS-PAGE of F2 and F1M2 fractions isolated from various species of *Polygonatum*, Yuzhu

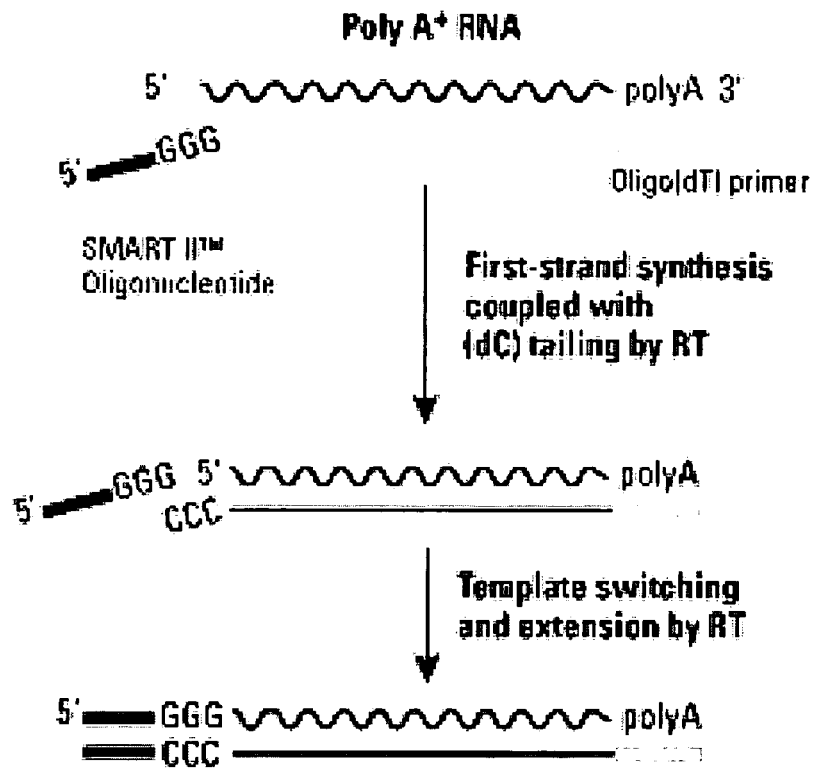
Fig. 4a Generation of first-strand cDNA
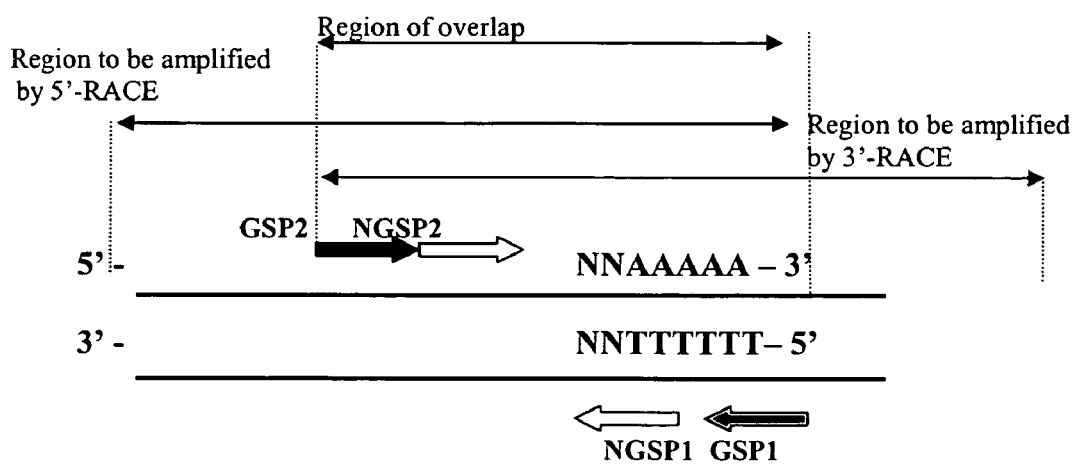
Fig. 4b GSP (gene specific primer) for 5' and 3' RACE

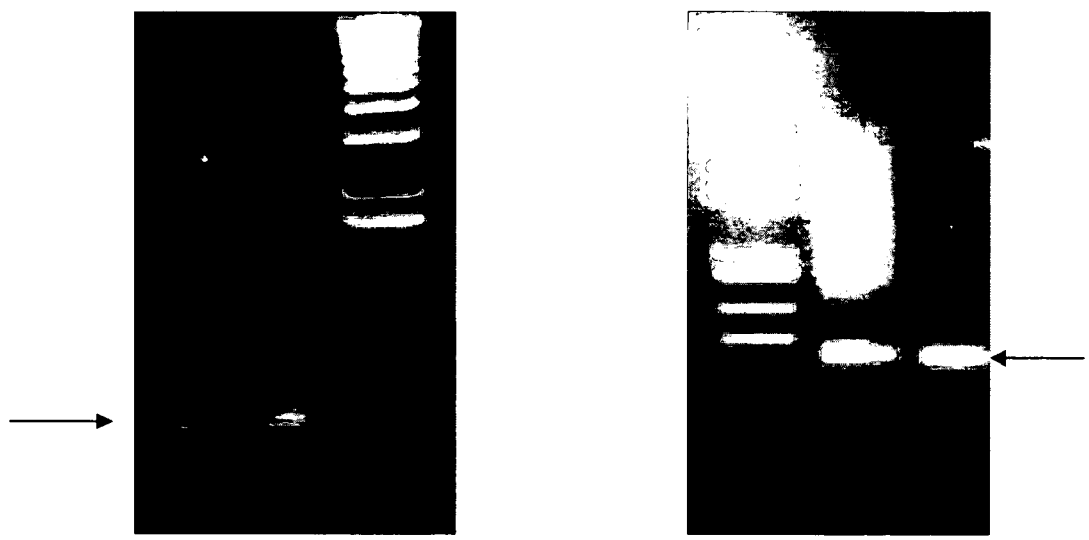
Fig. 4c 5' RACE of POL     Fig. 4d 3' RACE of POL
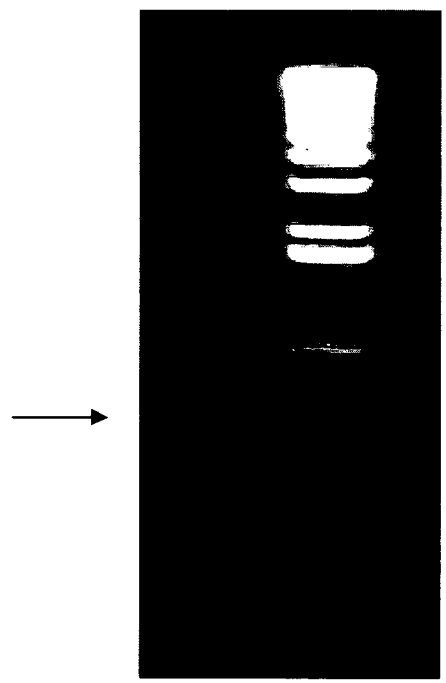
Fig. 4e Amplification of the POL open reading frame

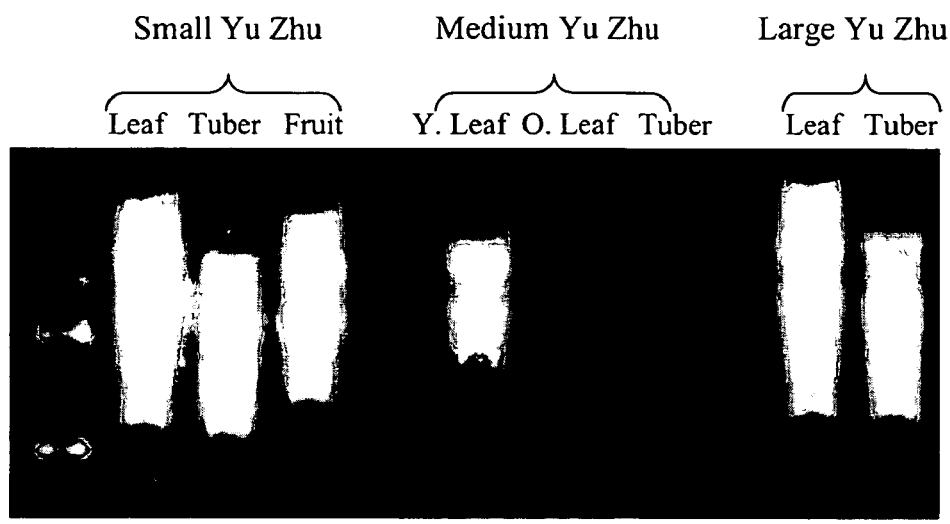
Fig. 5a Spatial expression of POL, RNA electrophoresis
Fig. 5b Spatial expression of POL, Northern blot analysis 1.
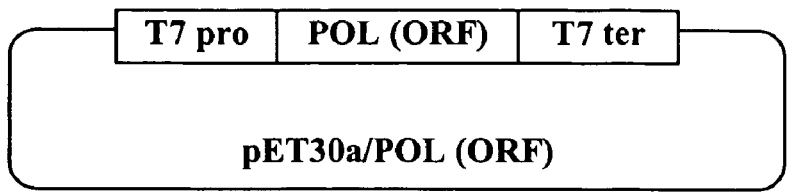
2.
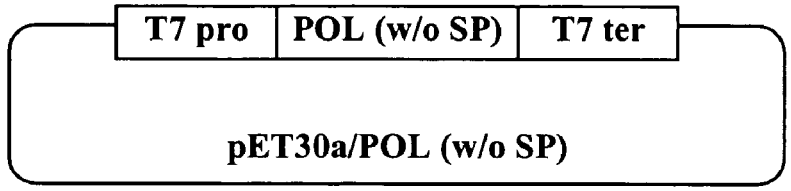
3.
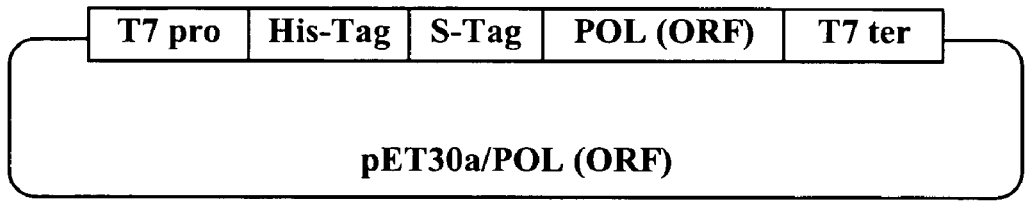
4.
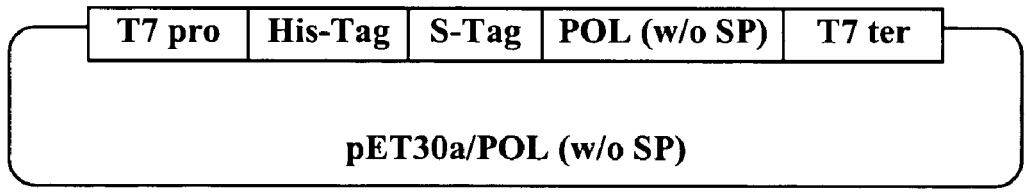
5.
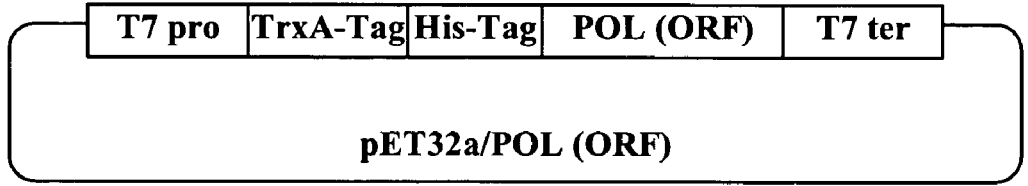
6.
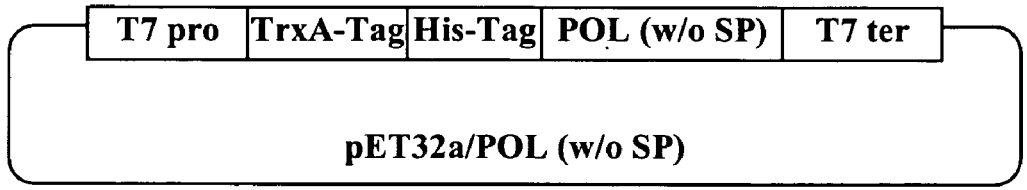
Fig. 6a Six constructs in pET-Vector systems

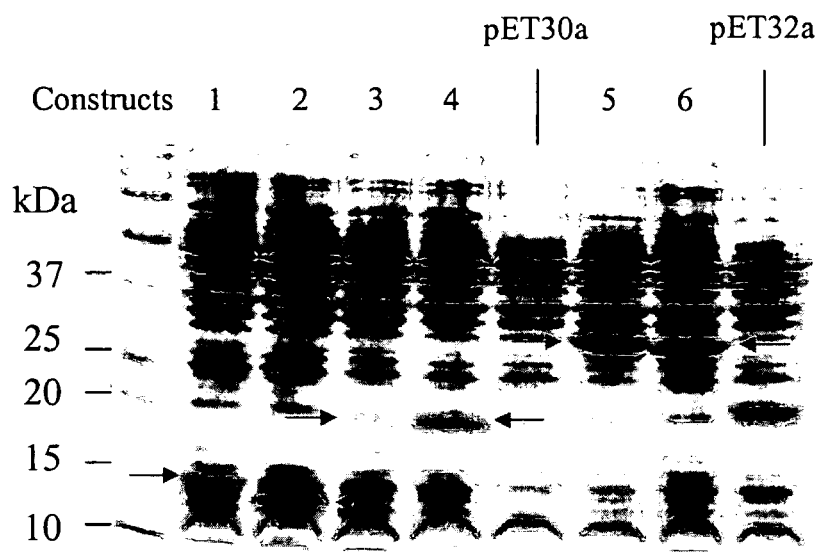
Fig. 6b Protein expression profile of recombinant POL, SDS-PAGE
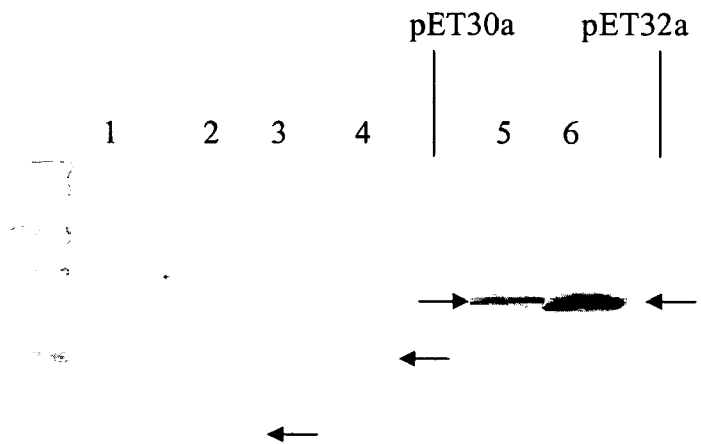
Fig. 6c Protein expression profile of recombinant POL, Western nlot analysis

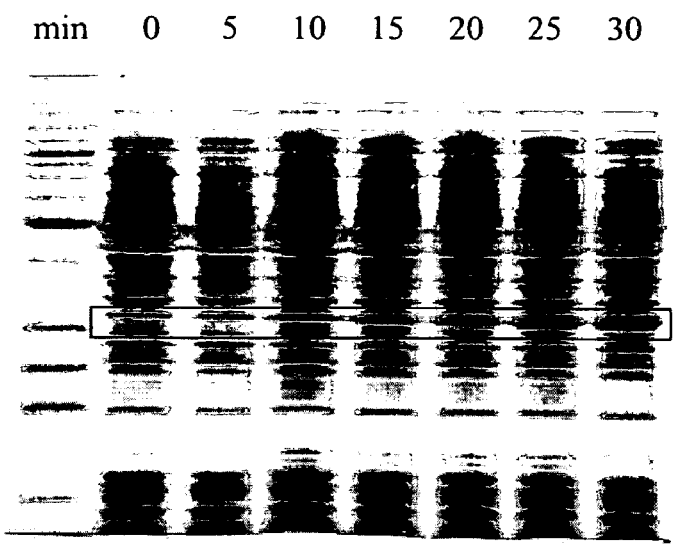
Fig. 6d IPTG induction time courses
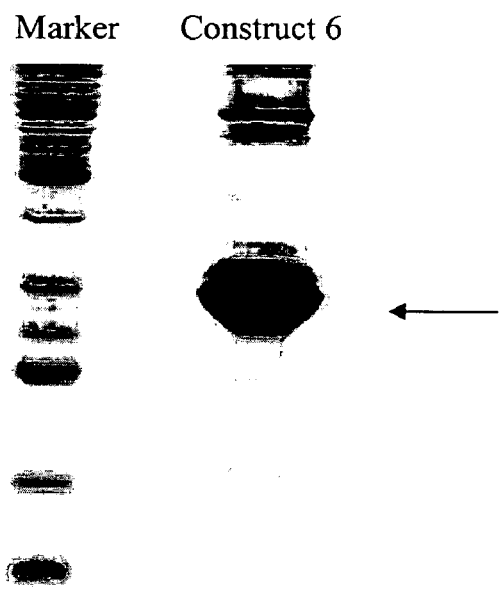
Fig. 7 POL from inclusion bodies 1) pSB130/Gt1/SP_POL/POL/Nos (Gt1/SP_POL/POL)

| Glutelin-1_pro | SP_POL | POL | NOS_ter |
|---|---|---|---|

2) pSB130/Gt1/SP_Gt1/POL/BP-80/Nos (POL/BP-80)

| Glutelin-1_pro | SP_Gt1 | POL | BP-80_CT | BP-80_TMD | NOS_ter |
|---|---|---|---|---|---|

3) pSB130/Gt1/SP_Gt1/AB-POL/Nos (AB-POL)

| Glutelin-1_pro | SP_Gt1 | Glutelin acidic unit | Basic | POL | unit | NOS_ter |
|---|---|---|---|---|---|---|

Fig. 8a  Structures of Glutelin-1 promoter constructs

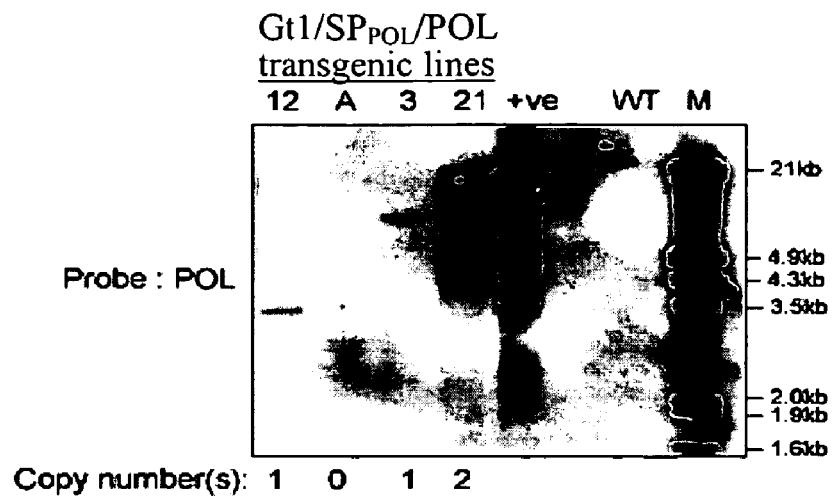
Fig. 8b Southern blot analysis of construct 1 Gt1/SP$_{POL}$/POL
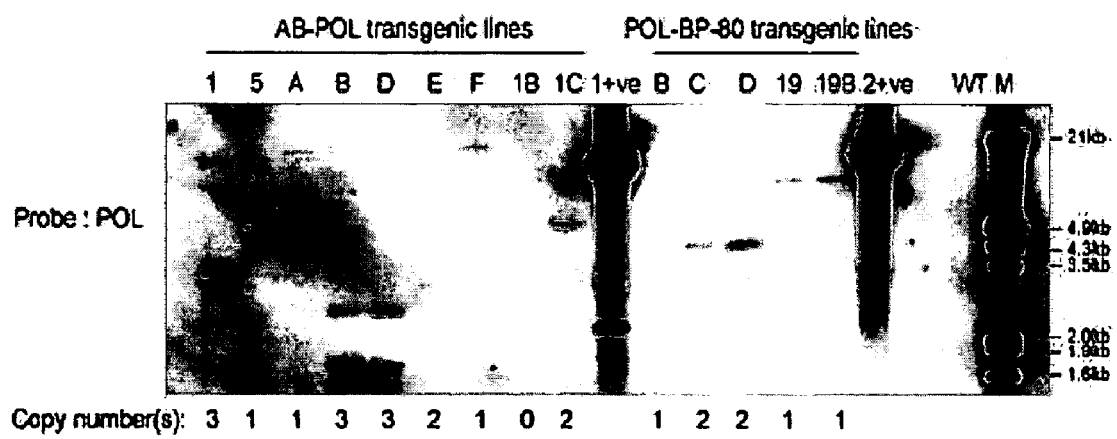
Fig. 8c Southern blot analysis of construct 2 Gt1/SP$_{Gt1}$/ POL –BP-80 (right) and construct 3) Gt1/SP$_{Gt1}$/AB-POL (left)

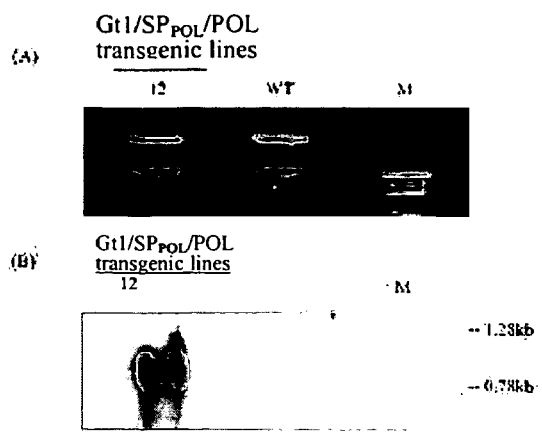
Fig. 8d Northern blot analysis of construct 1Gt1/SP$_{POL}$/POL
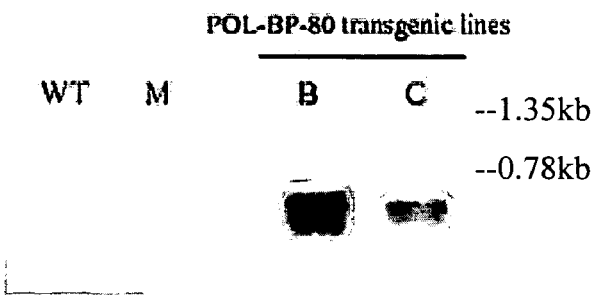
Fig. 8e Northern blot analysis of construct 2 Gt1/SP$_{Gt1}$/ POL –BP-80
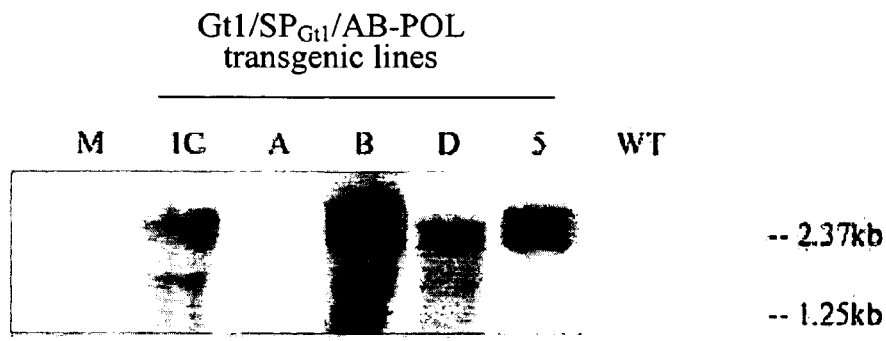
Fig. 8f Northern blot analysis of construct 3 Gt1/SP$_{Gt1}$/AB-POL

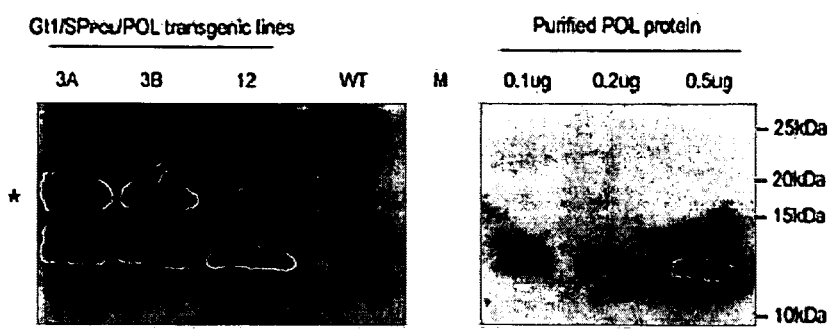
* indicates
Fig. 8g Western blot analysis of construct 1 Gt1/SP$_{POL}$/POL
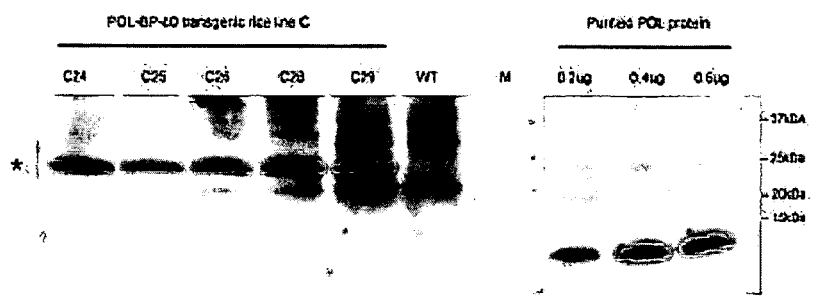
* indicates
Fig. 8h Western blot analysis of construct 2 Gt1/SP$_{Gt1}$/ POL –BP-80
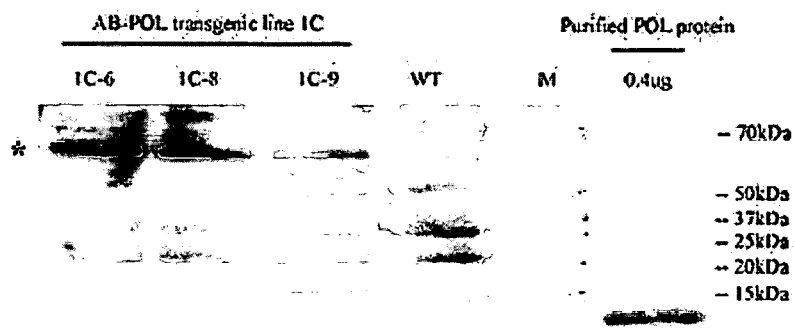
* indicates
Fig. 8i Western blot analysis of construct 3 Gt1/SP$_{Gt1}$/AB-POL

SEQUENCE LISTING

<160> NUMBER OF SEQ ID NOS: 1

<210> SEQ ID NO 1
<211> LENGTH: 483
<212> TYPE: DNA
<213> ORGANISM: Polygonatum odoratum

<400> SEQUENCE: 1

```
atggcagcta gtaatagttc aatcctcctg atcctcatgg ccaccatcgc catctttggc      60
ctcatggttg catcgccatg cgcagcggac aattctctga cctcccccaa cagcctcggc     120
tccggccatt ccctcgacac gggctcttac cgtgccatca tgcagggaga ctgcaactta     180
gtggtgtacg actcaggcaa acctgtttgg gcgtccaaca ccggcgggct cgcccgtgac     240
tgccgcttga cgttgcacaa caacgggaac ctcgtcatct acgataggag caaccgtgtg     300
atttggcaga ccaagacgaa cgggaaggag gaccactacg tgctggtgct gcagcaagac     360
cgcaatttgg tcatctacgg ccctgcagtc tgggccaccg gctctggacc ggccgtcgga     420 ctcaccct tg ttccgcataa cgttactgct attgttgatg ctagagcgat gcttaatgag     480
tag                                                                    483
```

ISOLATED PROTEINS FROM A TRADITIONAL CHINESE MEDICINE YUZHU AND USE THEREOF

BACKGROUND OF THE INVENTION

1. Technical Field of the Invention

This invention is directed to an extract of a plant and use thereof, particularly to an isolated protein from a traditional Chinese herbal medicine (TCM), Yuzhu, *Polygonatum odoratum* (Liliaceae) and use thereof.

2. Description of the Related Art

Yuzhu, *Polygonatum odoratum* (Mill) Druce, belonging to liliaceae, is a famous Chinese herbal medicine, and commonly found in dry to moist shaded areas where the soil is rich. This perennial stands one to three feet high at maturity, producing small, white, and bell-shaped flowers and dark purple fruits that hang from the leaf axils largely in pairs. The rhizome itself is edible, and has traditionally been used for treatment of coughing, fever and weakness due to malaise, and for treatment of hyperlipidemia, preventing cardiovascular disease and improvement of cardiac muscle due to the toxicity of digitalis, as well as treating paralysis due to stroke. Hence, it is widely cultivated in temperate regions of China, from Northern Guandong to Northern-east China provinces.

In the PRC Pharmacopoeia (2000), *Polygonatum odoratum* is an official plant species for Yuzhu (Rhizoma Polygonati Odorati). However, other related species have been also used as "Yuzhu" in the market. The criterion of quality control for Yuzhu, according to the PRC Pharmacopoeia, is the polysaccharide content in it. The content of polysaccharide is based on the glucose content (not less than 6% of its dry-weight) by sulfuric-phenol methods. However, the PRC Pharmacopoeia provides no data on the function of proteins.

In China, the firstly recorded use of Yuzhu might go back to the "Shen'nong Bencaojing" of the first century AD. It is considered a yin tonic, and is thought to be particularly applicable to problems affecting the digestive, respiratory and cardiovascular systems. Taking advantage of the long history of consumption by the Chinese to treat various diseases in the complex decoctions without any obvious adverse effect, the protein from this herb, therefore, can be considered relatively safe for human consumption.

SUMMARY OF THE INVENTION

Lectins play an important role in plant defense. Recently we have identified a few novel and potent antiviral lectins from relatively untapped traditional Chinese medicinal herbs. Chief among these, we have isolated antiviral proteins from commercially available dried herbs and fresh plants that are collectively used as Yuzhu, Rhizoma Polygonati Odorati, which has not been reported. The present invention thereby is provided.

The cDNA encoding for the newly purified antiviral proteins from the rhizomes of *P. odoratum* was cloned and provided in the present invention for transgenic application.

The present invention demonstrates the potent bioactivities of proteins from *P. odoratum* (POL) and related species which have been used as the Chinese herbal medicine, Yuzhu. The present invention is particularly useful as it provides the full-length cDNA clones encoding for POL from *P. odoratum*. They also provide a transgenic production system with promising potential to produce this useful protein in a large scale and much economical way through transferring the gene into bacteria, edible plants or crop seeds. The edible plants or crop seeds can be directly consumed by humans or animals for its biological activities.

The invention provides a protein and use of the same in the inhibition of cancer cells associated with proliferation and viruses such as flu viruses.

According to a first aspect of the present invention, there is provided a protein having a homological sequence with an amino acid sequence encoded by atggcagcta gtaatagttc aatcctcctg atcctcatgg ccaccatcgc
   catctttggc 60
ctcatggttg catcgccatg cgcagcggac aattctctga cctcccccaa
   cagcctcggc 120
tccggccatt ccctcgacac gggctcttac cgtgccatca tgcagggaga
   ctgcaactta 180
gtggtgtacg actcagcaa acctgtttgg gcgtccaaca ccggcgggct
   cgcccgtgac 240
tgccgcttga cgttgcacaa caacgggaac ctcgtcatct acgataggag
   caaccgtgtg 300
atttggcaga ccaagacgaa cggaaggag gaccactacg tgctggtgct
   gcagcaagac 360
cgcaatttgg tcatctacgg ccctgcagtc tgggccaccg gctctggacc
   ggccgtcga 420
ctcacccttg ttccgcataa cgttactgct attgttgatg ctagagcgat gct-
   taatgag 480
tag 483

(SEQ ID NO: 1).

A second aspect of the present invention is directed to a nucleic acid having a homological sequence of SEQ ID NO: 1.

According to a third aspect of the present invention, there is provided a DNA construct comprising a nucleic acid having a homological sequence of SEQ ID NO: 1 operably linked to a vector.

It is a fourth aspect of invention to provide a host cell expressing a DNA construct defined herein.

According to a fifth aspect of the present invention, there is provided a method for expressing a protein having a homological sequence with an amino acid sequence encoded by SEQ ID NO: 1 in a host cell, comprising:
   constructing a construct comprising a nucleic acid having a homological sequence of SEQ ID NO: 1 operably linked to a vector;
   transfecting the construct into a host cell; and
   harvesting and isolating the protein expressed by the construct in the host cell.

According to a sixth aspect of the present invention, there is provided a method of isolating a biologically active protein from a traditional Chinese medicine, Yuzhu, comprising:
   providing a material of Yuzhu;
   contacting the material with a NaCl solution to obtain a supernatant;
   adding to the supernatant ammonium sulfate to obtain a precipitate;
   dialyzing the precipitate in a distilled water to obtain a solution;
   lyophilizing the solution to obtain a crude protein; and
   subjecting the crude protein onto an agarose column to obtain a target protein.

A seventh aspect of the present invention is to provide a medicament comprising a therapeutically effective amount of a protein as defined herein.

According to an eighth aspect of the present invention, there is provided use of a protein as define herein in preparing a medicament for inhibiting cancer cells associated with proliferation or viruses.

According to a ninth aspect of the invention, there is provided a method for inhibiting cancer cells associated with proliferation or viruses, comprising contacting an effective amount of a protein defined herein with the cells or the viruses.

A tenth aspect of the invention is directed to a transgenic plant comprising a protein expressed by a nucleic acid having a homological sequence with SEQ ID NO. 1.

According to an eleventh aspect of the present invention, there is provided a functional food made from a transgenic plant defined herein.

In one embodiment of the present invention, the protein is isolated from Yuzhu, preferably having a retention time of 29.02±0.74 min in Superdex 75 HR 10/30 column. The isolated protein inhibits cancer cells associated with proliferation or viruses.

In a further embodiment of the invention, the protein has a subunit with a molecular weight of 14 kDa; preferably, the protein is a homodimer consisting of two subunits, having a molecular weight of 28 kDa.

In a preferred embodiment of the present invention, the nucleic acid has a sequence of SEQ ID NO. 1. And the protein is encoded by SEQ ID NO. 1.

The virus mentioned in the present invention preferably is selected from the group consisting of a Herpes simplex virus, a respiratory syncytial virus and an influenza-A virus, and the cancer cell includes an HL-60 cell and an MCF-7 cell.

Other aspects and objects of the invention will be described below in detail with reference to the accompanying drawings.

BRIEF DESCRIPTION OF THE DRAWINGS

FIG. 1a shows the chromatogram of an isolated protein of the invention POL (F2) on a fetuin-agarose column: F1: eluted by the equilibrium buffer, 45 mM Tris buffer (pH=8); F2: eluted by the eluting buffer, 50 mM glycine in, 0.5M NaCl (pH=3); Mark 1: the equilibrium buffer is applied; and Mark 2: the eluting buffer is applied.

FIG. 1b shows the chromatogram of an isolated protein of the invention POL (M2) on a mannose-agarose affinity column in which Mark 1: Mes buffer (20 mM, pH=6.2); Mark 2: 0.2M mannose in Mes buffer; and Mark 3: 2M NaCl.

FIG. 2 shows the chromatogram of an isolated protein of the invention POL (peak 2) on a Superdex 75 HR 10/30 column (Pharmacia), in which the eluting buffer is 0.1M ammonium bicarbonate (pH~8); and flow rate is at 0.4 ml/min. Peak 2 contains most of the M2 fraction, about 66.6% of the total protein loaded on the column. However, to ensure the purity, only tube 14 and 15 are collected. Tube 13 may be reloaded on the column for further purification.

FIG. 3a shows SDS-PAGE of M2 fraction before and after gel filtration on a Superdex 75 column, in which A: M2 after affinity column and before gel filtration and B: M2GF after gel filtration.

FIG. 3b shows SDS-PAGE of F2 fractions isolated from Yuzhu, in which A=*Polygonatum odoratum* var. Hunan; B=*Polygonatum odoratum* var. Hubei; C=*Polygonatum odoratum* var. Guangdong; D=*Polygonatum odoratum* dried TCM; and F2=fraction binding to the fetuin-agarose column.

FIG. 3c shows SDS-PAGE of F2 fractions isolated from Yuzhu, in which A=*Polygonatum odoratum* var. Hunan; B=*Polygonatum odoratum* var. Hubei; C=*Polygonatum odoratum* var. Guangdong; D=*Polygonatum odoratum* dried TCM; F1M2=M2 fraction from the fraction not binding to fetuin-agarose column; and F2=the fraction binding to the fetuin-agarose column.

FIG. 4a shows generation of the first-strand cDNA of the invention.

FIG. 4b shows GSP for 5' and 3' RACE, in which GSP: a gene specific primer and NGSP: a nested gene specific primer. Both are designed based on conserved cDNA regions.

FIG. 4c shows 5'RACE of POL, in which a ~500 kb specific band is amplified by 5' RACE (indicated by an arrow).

FIG. 4d shows 3' RACE of POL, in which a ~400 kb specific band is amplified by 3' RACE (indicated by an arrow).

FIG. 4e shows an electrophoresis of an amplification of the POL open reading frame. By eliminating the 5' and 3' untranslated regions (UTR), the open reading frame (ORF) of POL is amplified using the primers specific to the start and stop codon sequences. The ORF represents a 483 bp POL coding sequence with multiple family members.

FIG. 5a shows an RNA electrophoresis of a spatial expression of POL, in which total RNA extracted from different plant vegetative organs of three Yuzhu species is separated by agarose gel electrophoresis (Y=young; O=old).

FIG. 5b shows spatial expression of POL, northern blot analysis. POL open reading frame is used as the probe. Signals are detected in particularly the tubers of the three Yu Zhu samples. This suggests that POL is strongly expressed particularly in the rhizomes but weakly in other vegetative organs like leaves and fruit.

FIG. 6a shows six constructs in pET-vector systems.

FIG. 6b shows protein expression profile of recombinant POL, SDS-PAGE. After bacterial induction, all the six constructs samples are loaded and run through SDS-PAGE. pET30a and pET32a are the controls that contain background bacterial proteins after induction. The arrows indicate the putative POL bands.

FIG. 6c shows protein expression profile of recombinant POL, western blot. The SDS-PAGE in (a) is further studied by western blot using anti-POL primary antibodies so as to verify the putative bands. The black arrows indicate specific signals. Only constructs 2, 4, 5 and 6 give positive signals.

FIG. 6d shows IPTG induction time course. SDS-PAGE of construct 6 recombinant POL at 5 minutes interval is studied. The red box highlighted the putative POL bands. The band becomes denser gradually and reaches a maximum at 25 minutes.

FIG. 7 shows POL from inclusion bodies. SDS-PAGE of construct 6 recombinant POL after inclusion body extraction was studied. The putative POL protein was enriched.

FIG. 8a shows structures of glutelin-1 promoter constructs, in which Glutelin-1pro: a Glutelin-1 promoter; $SP_{POL}$: a signal peptide sequence of POL cDNA; $SP_{Gt1}$: a signal peptide sequence of a gluteline-1 gene; BP-80: a binding protein-80 kDa; CT: a cytoplasmic tail; and TMD: a transmembrane domain.

FIG. 8b shows Southern blot analysis of construct 1 Gt1/SPPol/POL, in which WT: wild type *japonica* (culitvar 9983); +ve: a positive control, plasmid pSB 130/Gt1/SP-POL/POL; and M: DNA molecular weight marker III, DIG-labeled (Roche).

FIG. 8c shows Southern blot analysis of construct 2 Gt1/SPGt1/POL-BP-80 (right) and construct 3 Gt1/SPGt1/AB-POL (left), in which WT: a wild type *japonica* (culitvar 9983); 1+ve: a positive control, plasmid pSB130/Gt1/SPGt1/AB-POL/Nos; 2+ve: a positive control, plasmid pSB130/Gt1/SPGt1/POL/BP-80CT/BP-80TMD/Nos; and M: DNA molecular weight marker III, DIG-labeled (Roche).

FIG. 8d shows Northern blot analysis of construct 1 Gt1/SP$_{Pol}$/POL, in which (A): 4 μg of rice seed total RNA is resolved in 1% agarose/formaldehyde gel; (B): Northern blot analysis of transgenic rice by using POL cDNA as a probe; 12: a Gt1/SP$_{POL}$/POL transgenic line; WT: a wild type *japonica* (cultivar 9983); and M: a 0.15 kb-1.77 kb RNA ladder (Invitrogen).

FIG. 8e shows Northern blot analysis of construct 2 Gt1/SPG$_{t1}$/POL-BP-80, in which B and C: POL-BP-80 independent transgenic lines; D and G: POL-a-TIP independent transgenic lines; WT: wild type *japonica* (cultivar 9983); and M: a 0.15 kb-1.77 kb RNA ladder (Invitrogen).

FIG. 8f shows Northern blot analysis of construct 3 Gt1/SP$_{Gt1}$/AB-POL using POL cDNA as a probe, in which 1C, A, B and 5: independent transgenic lines; WT: wild type *japonica* (cultivar 9983); and M: a 0.24 kb-9.5 kb RNA ladder (Invitrogen). B and D belong to same transgenic line.

FIG. 8g shows Western blot analysis of construct 1 Gt1/SP$_{Pol}$/POL, in which 3A and 3B: 2 rice seeds of transgenic line No. 3; 12: Rice seed of transgenic line No. 12; WT: wild type *japonica* (cultivar 9983); and M: Precision Plus Protein Dual Color Standards (Bio-Rad).

FIG. 8h shows Western blot analysis of construct 2 Gt1/SP$_{Gt1}$/POL-BP-80, in which C24-26, C28-29: 5 independent rice seeds of transgenic line C; WT: wild type *japonica* (cultivar 9983); and M: Precision Plus Protein Dual Color Standards (Bio-Rad).

FIG. 8i shows Western blot analysis of construct 3 Gt1/SP$_{Gt1}$/AB-POL, in which 1C-6, 1C-8 and 1C-9: 3 rice seeds of transgenic line IC; WT: wild type *japonica* (cultivar 9983); and M: Precision Plus Protein Dual Color Standards (Bio-Rad).

DETAILED DESCRIPTION OF THE INVENTION

The above-mentioned aspects and other aspects of the present invention will be further described in detail with reference and drawings.

Definitions

The term "Yuzhu" referred to in the invention means a plant belonging to the species generally defined as a traditional Chinese medicine. In the invention, Yuzhu includes those coming from south China including Guangdong Province, Hunan Province and Hubei Province.

The term "POL" used in the invention is an abbreviation of *Polygonatum odoratum* lectin, and a synonym of an isolated protein from a plant of Yuzhu.

The "isolated protein" means a protein that is extracted and isolated from Yuzhu, with a potent bioactivity.

The term "homology" or "homological" used herein to define the identity or percent identity between two or more amino acids or nucleic acids, refers to two or more sequences or subsequences that are the same or have a specified percentage of amino acids or nucleotides that are the same, i.e., about 80% identity, preferably about 85%, 90%, or 95% identity over a specified region.

The first aspect of the invention provides a protein having a homological sequence with an amino acid sequence encoded by atggcagcta gtaatagttc aatcctcctg atcctcatgg ccaccatcgc catctttggc 60
ctcatggttg catcgccatg cgcagcggac aattctctga cctccccaa cagcctcggc 120 tccggccatt ccctcgacac gggctcttac cgtgccatca tgcagggaga ctgcaactta 180
gtggtgtacg actcaggcaa acctgtttgg gcgtccaaca ccggcgggct cgcccgtgac 240
tgccgcttga cgttgcacaa caacgggaac ctcgtcatct acgataggag caaccgtgtg 300
atttggcaga ccaagacgaa cgggaaggag gaccactacg tgctggtgct gcagcaagac 360
cgcaatttgg tcatctacgg ccctgcagtc tgggccaccg gctctggacc ggccgtcgga 420
ctcacccttg ttccgcataa cgttactgct attgttgatg ctagagcgat gct-taatgag 480 tag 483

(SEQ ID NO: 1). Preferably, the protein in the invention has an amino sequence encoded by SEQ ID NO: 1.

The inventors have gained an isolated protein from Yuzhu. The protein has a retention time of 29.02±0.74 min in a Superdex 75 HR 10/30 column on an FPLC system, which is considered a potent bioactive protein (POL).

The invention also provides a method for extracting an isolated protein from Yuzhu. Any kind of Yuzhu in the PRC Pharmacopoeia (2000) can be used as materials to be extracted, and preferably, a dried herbal material, Yuzhu from Guangzhou, Guangdong Province, China, is used.

The method of the extraction of the POL may include obtaining a crude protein and isolating an isolated protein. In some embodiments of the present invention, obtaining the crude protein generally includes but not to limit: homogenizing a sliced and dried material of Yuzhu with a NaCl aqueous solution; adding slowly ammonium sulfate to the resulting supernatant to make saturation; collecting the resultant precipitate; re-dissolving the precipitate in a distilled water; dialyzing the resultant solution extensively against a distilled water; and lyophilizing the resultant clear supernatant to yield a crude protein powder.

The bioactive protein (isolated protein) is then isolated from the crude protein. In the invention a chromatographic column such as an agarose column with specific affinity ligands and a Superdex column can be used for isolation. Though those skilled in the art can find out that other methods such as SDS-PAGE, conventional means suitable for isolating a protein from a composition containing the target protein, can be used in this procedure, the invention preferably uses affinity and size exclusion chromatographic columns.

More preferably, the invention applies two agarose columns. Generally, two purification strategies are applicable.

One is the application of combining a fetuin-agarose column with a mannose-agarose column. Firstly the crude protein is applied onto a column (5×1.5 cm) packed with fetuin-agarose such as a product from Sigma, U.S.A. to retrieve the bound protein, and then a column (5×1.5 cm) packed with mannose-agarose such as a product from Sigma, U.S.A. is used to separate the unbounded protein from the fetuin-agarose column.

Alternatively, a mannose-agarose column is solely applied to retrieve the isolated protein from the crude protein.

The dual-column method is more preferred as a higher yield is obtained when compared to the mannose-agarose column alone. The total yield for the former is about 2% and the latter is about 1% of the total crude protein by weight.

The isolated protein of the invention has been confirmed having a molecular weight of 28 kDa by size exclusion gel filtration (Superdex), which is calibrated with a standard curve constructed by known standards. The Sodium dodecyl sulfate polyacrylamide gel electrophoresis (SDS-PAGE) results indicate that the isolated protein comprises two subunits of 14 kDa.

The method of Edman degradation combining a HPLC system is conventionally used to screen a sequence of an amino acid in the art. In the invention, a homology search for "identical" or "percent identity" is applied for determining an N-terminal amino acid sequence of the insolated protein.

The presence of carbohydrates in the POL of the invention is tested by periodic acid-Schiff (PAS) staining after western blotting onto an immobilized membrane (PVDF). The protein on PVDF membrane is first fixed in trichloroacetic acid (12.5%). The oxidation of the carbohydrate is performed by reacting with an oxidizing reagent containing 1% periodic acid in 3% acetic acid solution. The resulting membrane then is reacted with the basic Fuchsin-sulfite in Schiff's reagent (Sigma) in dark to yield a pink color complex against a white background (Ooi, 1998).

POL is therefore, not a glycoprotein as judged by its negative result of PAS staining.

The isolated protein of the present invention has been proved to inhibit infection of viruses such as flu virus, and proliferation of cancer cells. It is expected for those skilled in the art that those proteins having a homology with the isolated protein will have bioactivities similar to the isolated protein, that are intended to be involved in the invention.

Accordingly, the protein of the invention can be used as an active component of a medicament for inhibiting infection of viruses and cancer cells.

The medicament of the present invention comprises an effective amount of the protein defined in the invention. It is understood that the medicament of the invention may optionally comprise a pharmaceutically acceptable carrier.

Carriers that can be used in the invention are well known for those skilled in the art. Suitable carriers are selected upon a formulation of the medicament to be formed and an active component used therein.

The present invention provides a method for inhibiting infection of viruses in a subject comprising administrating an effective amount of a protein or an effective amount of a medicament defined herein to the subject.

As another aspect of the invention, it is to provide a method for inhibiting the growth of cancer cells comprising contacting an effective amount of a protein or an effective amount of a medicament of the invention with the cancer cells.

According to the invention, a method for expressing a protein defined herein in a host cell is provided. In order to express a target protein in host cells such as bacteria and plant cells, a gene of the protein shall be cloned. Preferably plant cells are used in the invention. Plant cells can be monocot or dicot.

Total RNA is isolated from different vegetative organs of Yuzhu including rhizomes, leaves, and fruit. There are many methods for isolating RNA from Yuzhu, for example, the phenol/chloroform extraction method, an RNAimage Kit (GenHunter Corporation, USA). Preferably, RNA is extracted from frozen grinded tissues using the phenol/chloroform extraction method in the invention. All the equipment and solutions used are treated by DiethylenePyrocarbonate (DEPC) so as to inhibit the RNase. The whole extraction process should be kept as low as 4° C. or on ice so as to reduce degradation rate. The quality of RNA is then verified by RNA gel electrophoresis or an Ultra spectrometer. The RNA samples are stored at least −70° C. for later RT-PCR and northern blot use. RNA should be extracted as quickly as possible when the plant tissues are freshly collected so as to maximize its quality.

The total RNA is taken to perform the Reverse Transcription-Polymerase Chain Reaction (RT-PCR) to amplify cDNA of a target protein. The first step in the amplification is the synthesis of a DNA copy (cDNA) of a region to be amplified (mRNA of the total RNA). Reverse transcription can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described in Romero and Rotbart in Diagnostic Molecular Biology: Principles and Applications pp. 401-406, Persing et al. eds., (Mayo Foundation, Rochester, Minn. 1993) and Egger et al., *J. Clin. Microbiol.* 33: 1442-1447 (1995).

It is proven to be difficult to obtain specific amplification product(s) using the degenerate primers. More specific information of the target gene is obtained by homology search in the genbank for similar mannose-binding lectins (MBLs) in different *Polygonatum* families. Two more homologous *Polygonatum* MBL genes are identified. They are from *P. multiflorum* (Van Damme et al., 1996) and *P. cyrtonema* (Bao et al., 2002) that share 83% similarity between their cDNA sequences. This similarity is then served as guidance in designing gene specific primers (GSP). In one embodiment of the invention, full-length POL cDNA is cloned using 5' and 3' Rapid Amplification of cDNA Ends (RACE) polymerase chain reaction (PCR) technique.

Since the monocot mannose-binding protein (MBL) is rather heterogeneous (Van Damme et al., 1996), the open reading frame (ORF) of the gene is identified rather than the highly variable 5' and 3' untranslated regions (UTRs). In the invention, the amplified products are introduced into a pGEM-T vector for sequencing, and among the heterogeneous members of the gene family cloned, the one with the highest homology to the two MBL family genes, from *P. multiflorum* and *P. cyrtonema* as deposited in the genbank, is chosen for further cloning and expression study.

In the invention, northern blot analysis is used for detecting the presence of the mRNA of spatial expression of the target gene, particularly the POL gene. It is understood that other methods, such as RT-PCR, and oligonucleotide array, can also be used to detect spatial expression of the gene.

Making use of a coding sequence of the target gene developed, the present invention provides a method to introduce the gene into an expression vector system for bacterial expression. In the invention, preferably a pET-vector system, such as pET30a and pET32a expression vectors, is employed, where pET32a contains a larger fusion-tag than pET30a so that a larger fusion construct could be generated.

The target gene cloned in the present invention can then be applied for the transformation to produce the target protein in transgenic plants, preferably in a portion of the plants which is edible by human or animals, particularly in plant seeds where expressed proteins can be stably accumulated. Accordingly, the present invention also provides a method of transforming the cloned cDNA into in a plant such as *japonica* rice by *Agrobacterium*-mediated transformation. We successfully demonstrate the transgenic integration and the expression of POL gene at mRNA and protein levels where the anti-viral activities of rice-derived POL protein is also confirmed. The present invention therefore, can be applied to produce bioactive proteins in a major staple crop for human and animal application. In an embodi-

EXAMPLES

Example 1

Isolation of Bioactive Proteins

I. Crude Extract (Protein) of Yuzhu

A sliced and dried material (250 g) of Yuzhu, *Polygonatum odoratum* (from Quangzhou, Quangdong, China) was homogenized with a 0.2M NaCl aqueous solution (2 ml/g). To the resulting supernatant was added slowly ammonium sulfate [$(NH_4)_2SO_4$, 561 g per liter] to make 80% saturation, and the resultant precipitate was collected. The precipitate was then dissolved in distilled water and the resultant solution was dialyzed extensively against distilled water of ten-time volume of the solution on the top of a magnetic stirrer at 4° C. for three cycles, at four hours per cycle where fresh distilled water was changed. The resultant clear supernatant was lyophilized to yield a crude protein powder (about 1.9 g).

II. Isolated with Fetuin Agarose Columns

For the best result, a crude protein powder (25 mg) as prepared in the above Part I was dissolved in 45 mM tris buffer (pH8.0) (25 ml) in such a way that the protein concentration is not over two milligram per ml and the solution was applied onto a column (5×1.5 cm) packed with fetuin-agarose (Sigma, U.S.A. Catalogue number F3256), which was previously equilibrated and eluted by the same buffer. After the unadsorbed proteins were eluted, the adsorbed proteins (F2) were eluted by 50 mM glycine in 0.5M NaCl (pH3). The unbound fraction, F1, was further used to isolate M2 by using a mannose-agarose column as described below in Tables 1b and 1c. Therefore, the total active compound (F2+F1M2) isolated was about 2.1% of the total extractable protein.

III. Isolated with Mannose Agarose Columns

For a viscous samples, more diluted solution is preferred to use in order to obtain the best result, such as a crude powder (15 mg) of an extract was dissolved in 23 ml of 20 mM Mes buffer (pH6.2), in which the protein concentration is not over one milligram per ml. The solution was applied onto a column (5×1.5 cm) packed with mannose-agarose (Sigma, U.S.A. Catalogue number M6400), which was previously equilibrated and eluted with the same puffer. After the unadsorbed proteins were eluted, the adsorbed proteins (M2) were eluted by 0.2M mannose in the eluting buffer.

TABLE 1a

| Fractions | Total Protein (mg) | |
|---|---|---|
| | Exp. 1 | Exp. 2 |
| Crude powder | 314 | 215 |
| M1 (non-mannose-binding protein) | 291.2 | 198.3 |
| M2 (mannose-binding protein I) | 3.74 | 4.32 |
| M3 (mannose-binding protein II) | 2.25 | 1.52 |
| Purified POL from M2 | 2.47 (0.8%)# | 2.85 (1.1%)# |

(% of the total extractable protein)

TABLE 1b

| Fractions | Protein Concentration (mg) | | Yield (%) | | Average Yield (%) |
|---|---|---|---|---|---|
| | Batch 1 | Batch 2 | Batch 1 | Batch 2 | |
| Crude Powder | 330.6 | 362.5 | — | — | |
| F1 | 312.3 | 302 | 94.5 | 83.3 | 88.9 |
| F2 | 1.83 | 2.02 | 0.55 | 0.56 | 0.56 |

TABLE 1c

| Fractions | Protein Concentration (mg) | | Yield (% of total F1 crude powder) | | Average (% of total F1 protein) | % of total extracted protein |
|---|---|---|---|---|---|---|
| | Batch 1 | Batch 2 | Batch 1 | Batch 2 | | |
| F1 Crude Powder | 269 | 273.8 | — | — | | 88.9 |
| F1M1 | 258.9 | 252.2 | 96 | 92.1 | 94 | 84 |
| F1M2 | 5.01 | 4.35 | 1.9 | 1.6 | 1.75 | 1.56 |

Example 2

Determination of Molecular Weight of Target Protein

I. By Gel Filtration (Size Exclusion)

Isolated compounds prepared in Example 1 were further purified on a Superdex 75 HR 10/30 column (Pharmacia Biotech) on an FPLC system, which was pre-equilibrated with ammonium bicarbonate buffer (100 mM, pH8) and calibrated with standard molecular markers (Sigma) including bovine serum albumin, carbonic anhydrase, cytochrome C, aprotinin and cytidine. The molecular weight of unknown was deduced from a standard curve constructed by the molecular weights (in log scale) and relative retention times on the column of the standards. A pure protein at a retention time of 29.02±0.74 min (Mean±S.D, n=12), as shown in FIG. 2, was collected and designated as POL. The molecular weight of POL appeared to be 28 kDA. The yield of POL was summarized in Tables 1a, 1b, and 1c.

II. By SDS-PAGE (Sodium Dodecyl Sulfate Polyacrylamide Gel Electrophoresis)

Sodium dodecyl sulfate polyacrylamide gel electrophoresis (SDS-PAGE) was carried out to check the purity of the isolated protein as detailed by Laemmli (1970). It was a discontinuous system with 15% separating gel (pH8.9) and 4% stacking gel (pH6.8). Prior to electrophoresis, all samples were boiled for 5 min with a sample loading buffer which contains SDS (2%) in the presence of 2-mercaptoethanol (2%). The samples run at a constant voltage (200V) in a mini electrophoresis system (Bio-Rad Mini-PROTEAN® II Elecrophoresis Cell and Power pack 300) for 48 min at room temperature. Coomassie Brilliant Blue R-250 was used to stain the gels for 30 min after electrophoresis.

As shown in FIGS. 3a, 3b, and 3c, POL was suggested to be a homodimer having a molecular mass of 28 kDa, which consisted of two subunits of 14 kDa.

Example 3

Analysis of N-Termination Amino Acid Sequence

POL separated on gel in Example 2 was blotted onto a polyvinylidene difluoride membrane (PVDF) in a modified Dunn's Buffer (consisted of 10 mM NaHCO$_3$, 3 mM Na$_2$CO$_3$, pH9.9, with 0.02% SDS) at a constant voltage (30V) in a mini trans-blot cell (Bio-Rad) for 1½ h at 4° C. The 14 kDa subunit was cut out and analyzed by an HP G1000A Edman degradation unit and an HP-1000 HPLC system.

Table 2 shows the N-terminal amino acid sequences of POL compared to some other monocot mannose-binding lectins in Families Alliaceae, Amaryllidaceae and Liliaceae wherein [1]ATL, *Allium tuberosum* lectin (Ooi et al., 2002); [2]ASA I, *Allium sativum* agglutinin domain I (VanDamme et al., 1992); [3]ACA, *Allium cepa* agglutinin (VanDamme et al., 1995); [4]GNA, *Galanthus nivalis* agglutinin (VanDamme et al., 1991); [5] NTL, *Narcissus tazetta* lectin (Ooi et al., 2000); [6]AAA, *Aloe arborescens* agglutinin (Koike et al., 1995); [7].POL, *Polygonatum odoratum* lectin, in the present study; [8].PMA, *Polygonatum multiflorum* agglutinin (VanDamme et al., 1996); [9].PCA, *Polygonatum cryptonema* agglutinin (Bao et al., NCBI data bank).

TABLE 2

| Families | Lectins | Sequences |
| --- | --- | --- |
| Alliaceae | ATL (JCT) | RNVLLNGEGLYAGQSLEVGHYKYIMQ DDDN (SEQ ID NO:2)[1] |
| Alliaceae | ATL(JC) | RNVLLNGEGLYAGQS (SEQ ID NO:3)[1] |
| Alliaceae | ATL(JH) | RNVLLNGEGLYAGQSLEVGH (SEQ ID NO:4)[1] |
| Alliaceae | ASA I | RNLLTNGEGLYAGQSLNVEPYHFIMQ EDCN (SEQ ID NO:5)[2] |
| Alliaceae | ACA | RNVLVNNEGLYAGQSLVVEQYTFIMQ FDCN (SEQ ID NO:6)[3] |
| Amaryllidaceae | GNA | DNILYSGETLSTGEFLNYGSFVFIMQ EDCN (SEQ ID NO:7)[4] |
| Amaryllidaceae | NTL | DNILYSGETLYSGQFLNYGDYRFIMQ ADDN (SEQ ID NO:8)[5] |
| Liliaceae | AAA | DNILYSSEVLHENQYISYGPYEFIMQ HDCN (SEQ ID NO:9)[6] |
| Liliaceae | POL | <u>DNSLTSPNSLPSGHSLNTGS</u>YRAIM (SEQ ID NO:10)[7] |
| Liliaceae | PMA | <u>DNSLTSPNSLPSGHSLNTGS</u>VRLIM (SEQ ID NO:11)[8] |
| Liliaceae | PCA | VNSLSSPNSLFTGHSLEVGPSYRLIM (SEQ ID NO:12)[9] |

Example 4

Clonings

I. RNA Isolation from Plant Tissues

Total RNA was isolated respectively from different vegetative organs of Yuzhu including rhizomes, leaves, and fruit. It was extracted from the frozen grinded tissues (*Polygonatum odoratum* var. Quangdong) using the phenol/chloroform extraction method (Altenbach et al., 1989). The quality of RNA was then verified by RNA gel electrophoresis. The RNA samples were stored at −80° C. for later RT-PCR and northern blot use.

II. Cloning of cDNA Encoding *Polygonatum odoratum* Lectin (POL)

The total RNA was taken to perform the Reverse Transcription-Polymerase Chain Reaction (RT-PCR) to regenerate the first-strand cDNA. This synthesis was coupled with the use of the MMLV Reverse Transcriptase —H⁻ mutant that acts as a terminal transferase to add 3 to 5 nucleotide residues (predominantly dC) to the 3' end of the first-strand cDNA. The dC short oligonucleotide can facilitate subsequent amplification using the kit's oligo G-ended primers (SMART™ RACE cDNA Amplification Kit, Clonetech Co., Catalogue no. K1811-1) (FIG. 4a).

Referring to FIG. 4b, gene specific primers (GSP) were designed based on the conserved sequences between *P. multiflorum* and *P. cyrtonema* MBL. Partial cDNAs (~300 bp specific band) were cloned from RT-PCR using the first 6 N-terminal amino acids sequence and the GSP. Based on the partial cDNA sequence, full-length cDNA was cloned using 5' and 3' Rapid Amplification of cDNA Ends (RACE) polymerase chain reaction (PCR) technique, (SMART™ RACE cDNA Amplification Kit, CLONTECH), as shown in FIGS. 4c and 4d.

Both the 5' and 3' untranslated regions (UTR) were amplified too, but since they were highly unconserved, only the open reading frame (ORF) was cloned by identifying the start and the stop codons (FIG. 4e).

Two primers (5'POL: 5' ATC TAC ATA TGG CAG CTA GTA ATA GTT C 3'; 3'POL: 5'GTA TAC GGA TCC TAC TCA TTA AGC ATC GCT C 3') (SEQ ID NOS: 13 and 14, respectively) were designed for amplifying the open reading frame of POL cDNA. The PCR reaction was carried out in a 25 µl reaction mixture (0.2 µg DNA template, 1 µM 5' Primer, 1 µM 3' Primer, 1×PCR buffer, 1 mM MgCl$_2$, 0.1 mM dNTPs, 2.5 Unit Taq polymerase) under the following reaction conditions: 94° C. for 5 minutes, then 25 cycles at 94° C. for 30 seconds, 56° C. for 30 seconds and 72° C. for 1 minute, followed by 1 cycle of 72° C. for 7 minutes.

The amplified products were introduced into a pGEM-T vector for sequencing. Twelve random clones were isolated and sequenced. They were found to slightly differ from each other for only a few base pairs. The clone with the highest homology to *P. multiflorum* and *P. cyrtonema* MBL was chosen for further cloning and expression, of which the sequence was illustrated as SEQ ID No. 1.

Example 5

Expressions

I. Spatial Expression Assay

Spatial expression of the POL gene was studied after cloning the POL cDNA. RNA electrophoresis was performed, where 6 µg of total RNA from different tissues was denatured, separated in 1% agarose gel, and blot hybridized using the DIG-labeled POL ORF as probes. An RNA ladder (0.24-9.5 kb) was used as a marker.

Northern blot analysis showed that signals were detected in particularly the tubers of all the three Yuzhu varieties, *P odoratum* var. Guangdong (Small Yuzhu), *P odoratum* var. Hunan (Medium Yuzhu), and *P odoratum* var. Hubei (Large Yuzhu), but not in other organs like leaves and fruit. The POL mRNA had a size of ~700 bp (FIGS. 5a & 5b).

Example 6

Characterization of Potent Bioactive Protein (POL)

Protein (POL) purified from a traditional Chinese herbal medicine, Yuzhu showed potent antiviral activities against Herpes Simplex Viruses (HSV-1, HSV-2), respiratory syncytial virus (RSV), and influenza-A virus and a potential inhibitory agent against avian influenza virus (bird Flu virus H5N1).

I. Hemagglutinating Test

The assay was carried out in a U-shape microtiter plate as described previously (Ooi et al., 1998). The hemagglutination titer is defined as the reciprocal of the highest dilution exhibiting hemagglutination and is equivalent to one hemagglutination unit. Specific hemagglutinating activity was expressed as the number of hemagglutinating units per mg protein in Table 3. Rabbit, human (ABO groups), and chicken red blood cells were used for hemagglutinating test. Concanavalin A (ConA) was used as a positive control, and phosphate-buffered saline (PBS, 0.1M, pH7.4) as a negative control. A serial twofold dilution of the lectin solution (in PBS) in microtitre U-plates (50 μl) was mixed with 50 μl of a 2% suspension of red blood cells in PBS at room temperature. The results were read after about one hour when the blank (with red blood cells and buffer only) had fully sedimented. The solutions of total crude protein (274 μg/ml), M1 (non-mannose-binding protein, 387 μg/ml), M2 (mannose-binding protein, 191 μg/ml) and purified POL (278 μg/ml) as well as ConA (800 μg/ml) were included in this study.

Table 3 indicated specific hemagglutinating activities of lectin-containing fractions in *Polygonatum ordoratum* (PO) as purification proceeded.

TABLE 3

| Fraction of PO on affinity column | Specific hemagglutinating activity (U/mg protein) for rabbit erythrocytes |
| --- | --- |
| Total crude protein | 584 |
| M1 (non-mannose-binding protein) | 413 |
| M2 (mannose-binding protein I) | 833 |
| Purified POL from M2 | 1143 |
| Control (ConA) | 12,800 |

From Table 3, POL was a weak agglutinin to rabbit erythrocytes when compared with ConA. However, neither human nor chicken blood was agglutinated.

II. Antiviral Activities

Antiviral activities of POL, virus control and positive controls were determined simultaneously by CPE (cytopathic effect) and/or plaque reduction assays using Vero cells (for HSV), Hep2 cells (for RSV), and MCDK cells (for FLU-A virus). $IC_{50}$ value is a protein concentration required to inhibit virus infection by 50%. Lower $IC_{50}$ value means less protein is needed to inhibit virus infection. Thus the lower the $IC_{50}$ value, the higher the antiviral activity.

1) Plaque Reduction Assay

Duplicate cultures of confluent Vero cells in 60 mm plastic dishes were infected with 100 plaque forming units (PFU)/0.2 ml of HSV-1, HSV-2 and RSV for 1 h at 37° C. in a humidified atmosphere with 5% $CO_2$. After removal of the inoculum, the cells were overlaid with 4 ml of a nutrient methylcellulose (0.8%) medium containing various doses of extracts (ranging from 1.55 μg/ml to 50 μg/ml), and incubated for 3 days at 37° C. The infected cells were fixed (with 10% formalin) and stained (with 1% crystal violet), and the number of plaques was counted. The $IC_{50}$ by plaque reduction assay for various strains of HSV-1, HSV-2 and RSV was summarized in Table 4. The $IC_{50}$ by plaque reduction assay for HSV-1 (15577), HSV-1 (Acyclovir resistant strain), HSV-1 (Clinical strain), HSV-2 (Clinical strain) and RSV (Long strain) was 2.6, 6.8, 9.5, 14.96 and 25 μg/ml, respectively.

Table 4 indicated the $IC_{50}$ by plaque reduction assay for various strains of HSV1, HSV2 and RSV.

TABLE 4

| Fractions | HSV-1 (15577) | Acyclovir resistant strain (HSV-1) $IC_{50}$ (μg/ml) | Clinical strain (HSV-1) | HSV-2 (clinical strain) | RSV (long strain) |
| --- | --- | --- | --- | --- | --- |
| M2 after crude extract on mannose-agarose affinity column | 2.1/3.0 with average of 2.6 | 6.8 | 9.5 | 14.96 | 25 |
| Positive control | ←———— Acyclovir (0.15) ————→ | | | Acyclovir (0.13) | Ribavirin (3.3) |

2) Cytopathic Effect (CPE) Inhibition Assay

Quadruplicate confluent monolayers of cells in 96-well plates were overlaid with serial twofold dilutions of the extracts (ranging from 1.55 μg/ml to 50 μg/ml) and equal volume of virus suspension [$10^3$ $TCID_{50}$/ml (50% Tissue Culture Infective Dose per ml)]. The virus induced CPE was scored on day 3 post-infection under an inverted phase-contrast microscope. The reduction of virus multiplication was calculated as % of virus control (% virus control=CPEexp/CPEvirus control×100). The concentration reducing CPE by 50% with respect to the virus control was estimated from the graphic plots and was defined as 50% inhibitory concentration ($IC_{50}$).

The antiviral activities of POL for dried TCM (Yuzhu) were summarized in Table 4a while those of fresh plants collected in the field were summarized in Table 4b. The potent protein demonstrated comparable antiviral effect to the current commercially available antiviral drugs. For example at the same experimental condition, the $IC_{50}$ of Acyclovir for HSV-1 and HSV-2 was found to be 0.25 μg/ml and 0.35 μg/ml by CPE method; and 0.15 μg/ml and 0.13 μg/ml by plaque reduction assay when tested in Vero cells. Beside, the $IC_{50}$ of Ribavirin for RSV was found to be 6.3 μg/ml by CPE method; and 3.3 μg/ml by plaque reduction assay when tested in Hep 2 cells.

Tables 4a-4b summarized the anti-viral results for Yuzhu, the dried TCM obtained from market and for fresh plants collected from field (by CPE method).

TABLE 4a

Yuzhu (Dried Herbs) $IC_{50}$ (μg/ml)

| Fractions | HSV-1 (15577) | Flu-A ($H_1N_1$) | RSV (long strain) |
|---|---|---|---|
| M2 after affinity column from crude protein extract | 2.10 | 6.25 | 25 |
| F2 after fetuin affinity column | 0.8 | 0.8 | 4 |
| M2 after F1 of fetuin-agarose column | 1.6 | 12.5 | 25 |
| Positive control | Acyclovir (0.25) | Ribvirin (6.3) | |

TABLE 4b

Yuzhu (Fresh Herbs) $IC_{50}$ (μg/ml)

| Fractions | HSV-1 (15577) | Flu-A | RSV |
|---|---|---|---|
| *P. odoratum* var. Hunan (Medium Yuzhu) | | | |
| F2 after fetuin affinity column | 2.1 | 1.6 | 8.3 |
| M2 after F1 of fetuin-agarose column | 1.6 | 12.5 | 6.3 |
| *P. odoratum* var. Guandong (Small Yuzhu) | | | |
| F2 after Fetuin affinity column | 2.1 | 1.6 | 50 |
| M2 after F1 of fetuin-agarose column | 0.8 | 0.4 | N/D |
| *P. odoratum* var. Hubei (Large Yuzhu) | | | |
| F2 after Fetuin affinity column | 2.4 | 3.1 | 6.3 |
| M2 after F1 of fetuin-agarose column | 0.4 | 0.4 | 3.0 |
| Positive control | Acyclovir (0.25) | Ribvirin (6.3) | |

3) Cytotoxicity Test

The in vitro cytotoxic effect of POL was tested using Vero cells. $2\times10^5$/ml cells were seeded into a well of the 96-well plate in 1% minimum essential medium (MEM) and incubated for 24 h. After 24 h all media were decanted and serial twofold dilutions of samples (in MEM) (ranging from 15.6 to 500 μg/ml) were added and incubated for another three days. MTT method was applied to determine the amount of viable cells. The cytotoxicity was expressed as 50% cytotoxic concentration ($CC_{50}$), which was the concentration of substances that inhibited up to 50% of growth of cells.

When MTT (3-[4,5-dimethylthiazol-2-yl]-2,5-diphenyl tetrazolium bromide) in the final concentration of 0.5 mg/ml was added to the culture, the cultures were further incubated for 3 h at 37° C. to allow the conversion of MTT to a formazan dye by mitochondrial dehydrogenase of the living cells. Thus, the assay assessed the ability of the test compound to inhibit the metabolic activity of mitochondrial dehydrogenase. The dye was measured at A540 nm with a multiscan plate reader using A690 nm as a reference.

The cytotoxic effect of POL to Vero cells was shown by its $CC_{50}$, which was about 156 μg/ml. Since its $IC_{50}$ was about 2.2 μg/ml, the selective index (SI) was 156/2.2=71.

4) Test for Virucidal Activity

To test for possible virucidal activity, the POL (50 μg/ml) was co-cultured with HSV-1 (15577) viruses [with PFU (plaque-forming unit) of $3.2\times10^6$] and incubated at 37° C. for one hour. After that the mixture was promptly diluted to $10^{-5}$ fold and assayed for residual viruses. The virucidal effect was determined by a plaque reduction assay. The data showed only 11-12% of viruses was inactivated.

5) Test for Effect of Pre-treatment of POL on Vero cells

The confluent Vero cells were incubated with the POL for 24 h at 37° C. at the concentrations of 12.5, 6.25, 3.125, 1.56 μg/ml, respectively. After incubation, the cells were washed twice with a culture medium to remove excess POL and followed by infecting with HSV-1 virus to allow the plaque formation. Cells that were not treated with POL were used as controls. The data showed that Vero cells were not protected from viral infection even in the presence of POL before viral infection. Therefore, the mechanism for the isolated protein to prevent the viral infection was different from that commonly shown by polysaccharides through the mechanism of adsorption to cells. Further mechanistic studies were required for its ability to inhibit viral infection.

6) Test for Lectin Inhibitors

Mannan (an oligosaccharide of mannose) is commonly used as one of the hapten inhibitors of hemagglutinating activity of mannose-binding lectins. When the co-existence of mannan (up to 25 μg/ml) with POL in the culture, the anti-viral (HSV-1) results were not affected. The data suggested that mannan itself had no ability to abolish the antiviral activity of POL, and thus it could not enhance or depress the replication of the virus.

III. Anti-proliferation Activity in vitro

Human leukemia HL-60 and human breast cancer MCF-7 cells were obtained from American Type Culture Collections (ATCC) (Rockville, Md.). All cultures were maintained according to the specifications from the ATCC. For suspension cancer cell line HL-60, cell concentration was adjusted to $1\times10^5$ cells/ml in growth medium, which will then be serially two-fold diluted with the sample material. The concentration will descend from 200 μg/ml to 0.78 μg/ml. Cell-sample mixture (100 μl) will be added to each well of a round-bottom 96-well plate. The plate was incubated at 37° C. in 5% $CO_2$ for 72 hours. After 72-hour incubation, the number of cells in each concentration of sample was determined by cell counts.

To evaluate the growth inhibitory effect of POL on MCF-7 cancer cell lines, MTT [4,5-dimethylthiazol-2-yl]-2,5-diphenyltetrazoliumbromide] assay was used as a quantitative colorimetric method for assessing cell growth and survival. Cells were plated in 96-well microtiter plates at a density of $2.5\times10^3$ cells/well/100 μl and treated either with various concentrations of POL, ranging from 6.25 to 200 μg/ml. After 72-h treatment, 10 μof MTT (5 mg/ml) was added to each well, and the incubation continued for 4 h at 37° C. Active mitochondrial dehydrogenases in living cells convert pale yellow tetrazolium salt, to dark blue formazan product. The precipitated formazan was solubilized with 150 μof HCl-isopropanol (0.04N) and the absorbance was determined at 570 nm. Mean and standard deviations were from triplicate data points. Independent experiments were repeated three times. The 50%-inhibitory concentration ($IC_{50}$) on MCF-7 cells for 72 h was determined.

POL had antiproliferative effect on HL-60 leukemia and MCF-7 cell lines in a dose dependent mode with $IC_{50}$ ranging from 150 to 200 μg/ml.

Preliminary test of POL for antiviral activity against avian flu (H5N1) showed that it had potential anti-H5N1 activity where the $IC_{50}$ was around 15-30 μg/ml.

Example 7

Expression of Bioactive Recombinant (POL) in Bacteria

I. Recombinant POL Constructs and Their Expression

Six constructs were designed (FIG. 6a):

pET30a:
1. T7 pro/POL(ORF)/T7 ter
2. T7 pro/POL(ORF w/o SP)/T7 ter
3. T7pro/His.Tag/S.Tag/POL(ORF)/T7ter
4. T7pro/His.Tag/S.Tag/POL(ORF w/o SP)/T7ter pET32a:
5. T7pro/TrxA-Tag/His-Tag/POL(ORF)/T7ter
6. T7pro/TrxA-Tag/His-Tag/POL(w/o SP)/T7ter All the six gene constructs were successfully expressed under IPTG induction. For the pET30a expression system, the non-fusion constructs 1 and 2 showed a major polypeptide of ~15 and 14 kDa, respectively, in SDS-PAGE where SP was removed in construct 2. For the fusion constructs 3 and 4, they gave a major band size of ~20 kDa, whereas the larger fusion constructs 5 and 6 in pET32a system encoded a ~30 kDa fusion POL (FIG. 6b). Signals were detected strongly in all the 3 constructs without SP, i.e. constructs 2, 4 and 6, but weakly or even no signal in constructs with SP, i.e. constructs 1, 3 and 5 (FIG. 6c). Also, the signals detected in the fusion constructs seemed to be stronger than that in the non-fusion one. The expression and detection profile were summarized in Table 5.

TABLE 5

| Gene Constructs | Putative protein band by SDS-PAGE | Western blot detection |
| --- | --- | --- |
| 1. T7pro/POL(ORF)/T7ter | ✓ | (Not detectable) |
| 2. T7pro/POL(w/o SP)/T7ter | ✓ | ✓ |
| 3. T7pro/His.Tag/S.Tag/POL(ORF)/T7ter | ✓ | (Uncertain) |
| 4. T7pro/His.Tag/S.Tag/POL(w/o SP)/T7ter | ✓ | ✓ |
| 5. T7pro/Trx.Tag/His.Tag/POL(ORF)/T7ter | ✓ | ✓ (Lower level) |
| 6. T7pro/Trx.Tag/His.Tag/POL(w/o SP)/T7ter | ✓ | ✓ |

II. Recombinant POL Expressed in Bacterial System

The POL was successfully expressed in pET bacterial system (Table 5). The six constructs were designed to study and characterize the differences in expression level between 1) fusion and non-fusion constructs and 2) in the presence and absence of a signal peptide sequence (SP). The results revealed that all the fusion constructs (3, 4, 5 and 6) have better expression and detection level then the non-fusion ones (1 and 2). Moreover, the larger fusion constructs (5 and 6) seemed to have even better results than the smaller ones (3 and 4). The present invention took advantage of the fusion protein strategy which helps stabilize the expressed protein and prevent the protein from degradation efficiently. On the other hand, we also demonstrated that in the signal peptide study, all the constructs without SP (2, 4 and 6) had a higher expression and detection level than those with SP (1, 3 and 5). The results suggested that the POL signal peptide sequence could lead to lower protein expression in bacterial system.

Construct 6 was used for the 0.1M IPTG induction time course study. One ml bacterial culture was removed and spun down at 5 minutes interval starting right after IPTG addition to the culture (time 0). The samples were analyzed by SDS-PAGE, and the putative POL band (~30 kDa) became denser and denser, finally reaching maximum at 25 minutes after induction (FIG. 6d). For the IPTG induction time course study, according to the pET expression system manual (Novagen), it was suggested that recombinant protein should be induced with 0.1M IPTG for 3 hours for the best result. However, the method provided by the present invention showed that the expression of recombinant POL could reach the maximum level in 25 minutes. This finding is supported by the recent work of Sanden et al. (2003), which reported that ribosomes and rRNA were additionally degraded (from 100% to 20%) upon induction due to the high recombinant production level. Translation therefore seemed to be the initial limiting factor of the protein synthesis capacity. Also, transcription analysis showed that β-galactosidase-specific messenger RNA was immediately formed after induction (<5 min), so the recombinant protein could be synthesized immediately after 5 minutes induction and reach maximum quickly due to limited amount of ribosomes.

For better transformation and expression result, 5 μl bacterial glycerol stock was inoculated in 5 ml LB broth and shaked at 37° C. for 16 hours. Then the inoculums were sub-cultured in 100 ml LB in 1:100 ration and shaked at 37° C. for 3 hours. IPTG (isopropyl-β-D-thiogalactopyranoside) was added to culture as a final concentration of 0.1M and followed by shaking for 3 h at 37° C.

III. Recombinant POL Antiviral Activity in vitro

The bioactivity of the recombinant POL was characterized. The antiviral activities of the recombinant POL in the crude fusion product were determined by the cyto-pathogenic effect (CPE) assay using various animal cell lines. The inclusion bodies of the bacteria were first isolated so as to enrich the recombinant POL. The extracted inclusion bodies were then passed through the mannose-affinity column to purify the recombinant proteins. The purified proteins were then used for CPE assay, where the proteins were incubated with the viruses being tested (HSV, RSV and FluA) in different cell lines so as to find out the $IC_{50}$ (50% inhibition concentration), the protein concentration requires to inhibit virus infection by 50%. This is achieved by microscopic inhibition observation. HSV and Flu A infection will cause a cell to change into round shape, whereas RSV infection will cause cell-cell fusion.

The recombinant POL was first isolated from the inclusion bodies after bacterial induction (FIG. 7). Constructs 1, 2 and 6 were studied in the CPE assay (Ooi et al., CUHK) so as to identify the effect of signal peptide as well as fusion protein on the antiviral activity ($IC_{50}$).

As showed in Table 6, the first two rows were the results of direct POL extraction from the plant tissues. The values of them were relatively low which means the antiviral activities towards the three viruses are quite high. The middle three rows were the results of the three recombinant POL constructs. Construct 6 exhibited a relatively lower antiviral activity; whereas constructs 1 and 2 had higher activities than construct 6, but still a bit lower than the direct POL extraction. The pET vector control proteins, without passing the column, in the last two rows showed that the bacterial background protein had no inhibition on HSV and Flu A, but had certain antiviral effect on RSV.

CPE assay was summarized in Table 6.

TABLE 6

| Protein Samples | *HSV | *Flu A | *RSV |
|---|---|---|---|
| Crude POL extracted from Yuzhu | 6.8 µg/ml | 6.25 µ/ml | 25 µg/ml |
| Crude POL extracted from small tuber (Small Yuzhu) | 2.1 µg/ml | 1.6 µg/ml | 50 µg/ml |
| Construct 6: pET32a/TrxA/His.Tag/POL(w/o SP) - cloned from small tuber | 125 µg/ml | 62.5 µg/ml | 250 µg/ml |
| Construct 1: pET30a/POL(ORF) - cloned from small tuber | 12.5 µg/ml | 25 µg/ml | 46.8 µg/ml |
| Construct 2: pET30a/POL(w/o SP) - cloned from small tuber | 50 µg/ml | 100 µg/ml | 46.8 µg/ml |
| pET 30a control protein | No activity | No activity | 31.3 µg/ml |
| pET 32a control protein | No activity | No activity | 16 µg/ml |

*$IC_{50}$ value
Small Yuzhu = *Polygonatum odoratum* var. Guangdong

In the functional assay, the antiviral activity of recombinant POL was tested by the CPE assay using Vero cells (for HSV), Hep2 cells (for RSV), and MCDK cells (for Flu-A virus). Quadruplicate confluent monolayers of cells in 96-well plates were overlaid with serial two fold dilutions of the extract of fusion or non-fusion construct product (ranging from 1.56 to 500 µg/ml) and equal volume of virus suspension [$10^3$ $TCID_{50}$/ml (50% Tissue Culture Infective Dose per ml)]. The virus induced CPE was scored on day 3 post-infection under an inverted phase-contrast microscope. The reduction of virus multiplication was calculated as % of virus control (% virus control=CPEexp/CPEvirus control ×100). The concentration reducing CPE by 50% with respect to the virus control was estimated from the graphic plots and was defined as 50% inhibitory concentration ($IC_{50}$). The three constructs (1, 2 and 6) being tested showed inhibition activity on all the three viruses (HSV, Flu A and RSV) (Table 6). Construct 6 is the fusion construct without SP and the activity of its product was a little bit lower when compared with the others. This could be because of the less amount of POL present in the fusion construct product when compared with the equal amount of the non-fusion one. Less amount of POL in the fusion construct means less mannose-binding sites, and thus less antiviral activity. For the non-fusion constructs (1 and 2), the antiviral activity towards the three viruses was quite high, but the $IC_{50}$ values were still nearly half that of the crude POL extraction.

Example 8

Expression of Bioactive POL in Staple Food

I. Recombinant POL Expression Constructs

Three constructs were designed as illustrated in FIG. 8a. All chimeric genes were driven by a Glutelin-1 promoter. The three constructs were designed as follows:
Construct 1): The POL cDNA with a signal peptide sequence was inserted between a Gt-1 promoter and a Nos terminator;
Construction 2): Protein targeting construct, where targeting sequences BP-80$_{CT}$ and BP-80$_{TMD}$ were inserted after POL cDNA in Construct 1; and
Construct 3): Glutelin fusion construct, where the POL was inserted in the middle of glutelin basic unit.

II. Recombinant POL Expression in Plant System

All chimeric genes constructed as in FIG. 8a were transformed into *Agrobacterium* EHA105. The transformed cells were spread on LB agar plate with 50 mg/L kanamycin. Single colony was picked from each construct and spread on another LB agar plate with 50 mg/L kanamycin. The single colonies on this plate were used for rice transformation.

The media and method used for plant transformation, preferably in staple food rice, are provided as follows. Immature seeds (10-15 days after flowering) were sterilized by immersing in 50% Chlorox and shaked for 90 minutes. Then, the seeds were washed by sterilized water for 8-10 times. The embryo was cut out from immature seeds and grown on $N_6D_2$ medium (Table 7) for 5 days in dark.

Table 7 showed media used for rice transformation and tissue culture.

TABLE 7

| Media | Medium Components |
|---|---|
| $N_6D_2$ | $N_6$ (Chu, 1978) nutrients and vitamins, casein hydrolase 0.5 g/L, sucrose 30 g/L, 2,4-D 2 mg/L, phytagel 2.5 g/L, pH 5.8 |
| $N_6D_2C$ | $N_6D_2$, glucose 10 g/L, AS 100☐mol/L, pH 5.2 |
| AAM | AA(Toriyama and Hinata, 1985) nutrients, MS(Murashige and Skoog, 1962) vitamins, casein hydrolase 0.5 g/L, glucose 36 g/L, sucrose 68.5 g/L, AS 100☐mol/L, pH 5.2 |
| $N_6D_2S$ | $N_6D_2$, Hygromycin B 50 mg/L, Cefotaxime 500 mg/L |
| MSR | MS nutrients and vitamins, casein hydrolase 0.3 g/L, sucrose 30 g/L, 6-BA 2 mg/L, NAA 0.5 mg/L, KT 0.5 mg/L, phytagel 2.5 g/L, Hygromycin B 50 mg/L, Cefotaxime 500 mg/L, pH 5.8 |
| MSH | ½ MS nutrients, MS vitamins, sucrose 30 g/L, NAA 0.5 mg/L, phytagel 2.5 g/L, Hygromycin B 50 mg/L, Cefotaxime 500 mg/L, pH 5.8 |

The single colony of *Agrobacterium* which carried the chimeric gene was inoculated in 3 ml LB medium with 50 mg/L kanamycin at 28° C. for 16 hours. Then, inoculums were cultured in AB medium in 1:100 ratio for 7 hours. Bacterial pellet was obtained by centrifugation and resuspended in AAM medium. The induced callus were immersed in this medium for 15 minutes and dried on sterilized filter papers. Subsequently, the calli were grown on $N_6D_2C$ (Table 7) for 3 days in dark.

The calli were then transferred to $N_6D_2S$ (Table 7) to select transformed cells for 2 weeks in dark. The selected calli were further grown on Higrow® Rice medium (GIBCOBRL) for 2 weeks: 1 week in dark and 1 week in 16 hours light continuous with 8 hours dark. After the pre-regeneration stage, the shoots were induced by putting callus on MSR medium (Table 7) with 16 hours light and 8 hours dark at 28° C. The regenerated shoots were transferred on rooting medium, MSH (Table 7), and after that, the whole plantlets were grown in greenhouse.

The integration of transgenes POL and HPT (hygromycin phosphotransferase gene) is confirmed by Southern analysis. The transgenic plants contain up to 3 copies of POL or HPT gene (FIG. 8b and FIG. 8c). To determine mRNA expression of target protein in immature rice seeds, 4 µg rice seed total RNA was collected from each independent transgenic lines and resolved in 1% agarose/formaldehyde gel. Northern blot analysis was carried out using POL cDNA as probes. mRNA expression of POL and fusion protein in immature rice seeds was detected in all three constructs (FIG. 8a, FIG. 8b and FIG. 8c).

Moreover, expression of POL and fusion proteins was detected by polyclonal rabbit anti-POL antibody and the expression level was estimated. 10 µg of rice seed total protein was resolved in Tricine SDS-PAGE for gel staining.

100 μg of resolved rice seed total protein was transferred to nitrocellulose membrane for detection by using polyclonal rabbit anti-POL antibody. To estimate the expression level, 0.2 μg-0.6 μg of purified POL protein were loaded together for comparison. Among the three constructs, construct 1) (FIG. 8g) and construct 3) (FIG. 8h) had the higher expression level of POL than construct 2) (FIG. 8i).

III. Recombinant POL Bioactivities in vitro

Total rice seed protein was extracted from $T_1$ seeds of construct 2) POL-BP-80. Two $T_1$ transgenic lines were chosen, B-2 and B-6. After extraction, seed protein was dialyzed extensively against distilled water to remove salts and SDS. Then, samples were freeze-dried for storage.

Table 8 indicated a summary of expression level of Glutelin-1 promoter constructs. All rice seeds tested in this table were from T0 transgenic plants, unless specified. Since the protein extraction buffer of AB-POL construct is different from other constructs, percentage of POL per total extractable protein cannot be estimated.

proteins demonstrate high biological activities. The recombinant POL protein can be economically produced for preparing pharmaceuticals and nutrients as well as potentially poultry feed for prevention of avian flu.

The present invention is not limited to the above description and examples. The preferred embodiments are offered by way of illustration and should not be interpreted as limitation to the scope of the invention. It is understood that those skilled in the art can make modifications and variations to the invention without departing from the spirit of the invention. The scope of the invention is defined in the appended claims.

REFERENCES

Altenbach, S. B., Pearson, K. W., Meeker, G., Staraci, L. C. and Sun, S. M. 1989. Enhancement of the methionine content of seed proteins by the expression of a chimeric gene encodings a methionine-rich protein in transgenic plant. *Plant Molecular Biology*, 13:513-522.

TABLE 8

| Constructs | Transgenic line | Copy number of transgene POL | Percentage of POL per total extractable seed protein (%) | Amount of POL in 1 gram mature seed (mg) |
|---|---|---|---|---|
| 1) Gt1/SP$_{POL}$/POL | 3 | 1 | 2.0 | 0.414-0.437 |
|  | 12 | 1 | 1.4 | 0.766 |
| 2) POL-BP-80 | B | 1 | 0.1-0.2 | 0.0260-0.0656 |
|  | C | 1 | 0.25-0.4 | 0.0737-0.0994 |
|  | B ($T_1$ seed) | 1 | 0.1-0.5 | 0.0291-0.105 |
| 3) AB-POL | A | 2 |  | 0.059-0.088 |
|  | B | 1 |  | 2.568-3.704 |
|  | 1C | 3 |  | 2.64-3.761 |

The bioactivity of the transgenic rice seeds was also studied and the recombinant protein demonstrated potent effect against three virus, HSV-1, RSV and influenza A virus where $IC_{50}$ of different samples against HSV, RSV and influenza A virus as estimated by CPE assay. Results from crude Yuzhu protein and *E. coli* expressed POL were also included for comparison (Table 9).

Table 9 showed the results of CPE assay of transgenic and wild type plant proteins.

TABLE 9

| | $IC_{50}$ against virus | | |
|---|---|---|---|
| Samples | HSV-1 (μg/ml) | RSV (μg/ml) | Flu A (μg/ml) |
| POL extracted from Yuzhu | 6.8 | 25 | 6.25 |
| (1) Bacterial POL protein purified by mannose-agarose column | | | |
| pET30a/SP$_{POL}$/POL | 12.5 | 46.8 | 25 |
| pET30a/POL | 50 | 100 | 46.8 |
| pET30a vector | — | 31.3 | — |
| (2) Total extractable rice protein | | | |
| WT | — | 188 | — |
| 6-B-2 ($T_1$ seeds) | 66 | 37.5 | — |
| 6-B-5 ($T_1$ seeds) | 31.5 | 18 | 18 |

Therefore, the present invention provides a purified potent bioactive protein (POL), and a POL protein encoding gene demonstrating a high expression level in bacteria and rice while both bacterial- and rice-derived recombinant POL Bao, J., Lu, H., Wu, C., Gong, M., Zhang, X. and Chen, F. 2002. Gene Bank Accession no.:AY099150

Chu, C. C. 1978. The $N_6$ medium and its applications to other culture of cereal crops. *In: Proceedings of Symposium in Plant Tissue Culture Science press*, Peking, pp 43-50.

Koike, T., Titoni, K., Suzuki, M., Beppu, H., Kuzuya, H., Maruta, K., Shimpo, K. and Fujita, K. 1995. The complete amino acid sequence of a mannose-binding lectin from "Kidachi aloe" (*Aloe arborescens* var. natalensis Berger). *Biochemical and Biophysical Research Communication*, 214: 163-170.

Laemmli, U. K. 1970. Cleavage of structural proteins during the assembly of the head of bacteriophage T4. *Nature*, 227: 680-685

Ooi, L. S. M 1998. Isolation, characterization and cloning of lectins from the Chinese daffodil *Narcissus tazetta* var. *chinensis* Ph.D. thesis, the Chinese University of Hong Kong.

Ooi, L. S. M., Ng, T. B., Geng, Y. Q. and Ooi, V. E. C. 2000b. Lectins from bulbs of the Chinese daffodil *Narcissus tazetta* (family Amaryllidaceae). *Biochemistry and Cell Biology*, 78: 463-468

Ooi, L. S. M., Sun, S. S. M., Ng, T. B. and Ooi, V. E. C. 2001. Molecular cloning and the cDNA-derived amino acid sequence of *Narcissus tazetta* isolectins. *Journal of Protein Chemistry* 20: 305-310.

Ooi, L. S. M., Ng, T. B. Sun, S. S. M. and Ooi, V. E. C. 2000a. Mannose-Specific Isolectins with Different Hemagglutinating Potencies Isolated from Chinese Daffodil (*Narcissus tazetta* var. *chinensis*) Leaves. *Journal of Protein Chemistry*, 19:163-167

Ooi, L. S. M., Wang, H., Ng, T. B. and Ooi, E. C. 1998. Isolation and characterization of a mannose-binding lectin from leaves of the Chinese daffodil *Narcissus tazetta*. *Biochemistry and Cell Biology*, 76: 601-608

Ooi, L. S. M., Yu, H., Chen, C. M., Sun, S. S. M. and Ooi, V. E. C. 2002. Isolation and characterization of a bioactive mannose-binding protein from the Chinese chive *Allium tuberosum*. *Journal of Agricultural and Food Chemistry*, 50: 696-700.

Toriyama and Hinata, 1985. Cell suspension and protoplast culture in rice. *Plant Science*, 41: 179-183.

Van Damme, E. J. M., Barre, A., Rouge, P., Van Leuven, F., Balzarini, J. and Peumans, W. J. 1996. Molecular cloning of the lectin and a lectin-related protein from common Solomon's seal (*Polygonatum multiflorum*). *Plant Molecular Biology*, 31: 657-672.

Van Damme, E. J. M., Kaku, H., Perini, F., Goldstein, I. J., Peeters, B., Yagi, F., Decock, B., and Peumans, W. J. 1991. Biosynthesis, primary structure and molecular cloning of snowdrop (*Galanthus nivalis* L.) lectin. *European Journal of Biochemistry*, 202: 23-30

Van Damme, E. J. M., Smeets, K. and Peumans, W. J. 1995. The mannose-binding monocot lectins and their genes. In "*Lectins, Biomedical Perspectives*" Pusztai, A. and Bardocz, S. Eds., p. 67, Taylor & Francis Van Damme, E. J. M., Smeets, K., Torrekens, S., Van Leuven, F., Goldstein, I. J. and Peumans, W. J. 1992. The closely related homomeric and heterodimeric mannose-binding lectins from garlic are encoded by one-domain and two-domain lectin genes, respectively. *European Journal of Biochemistry*, 206: 413-420

What is claimed is:

1. An isolated and purified nucleic acid comprising the sequence of SEQ ID NO: 1.

2. A DNA construct comprising an isolated nucleic acid comprising the sequence of SEQ ID NO: 1 operably linked to a vector.

3. The DNA construct of claim 2, wherein the vector is a pET vector.

4. A host cell expressing a DNA construct of claim 2.

5. The host cell of claim 4, wherein the host cell is a bacterial cell or a plant cell.

6. The host cell of claim 5, wherein the plant cell is a monocot or a dicot.

7. A method for expressing an isolated and purified protein comprising the amino acid sequence encoded by SEQ ID NO: 1 in a host cell, comprising:

constructing a construct comprising a nucleic acid having the sequence of SEQ ID NO: 1 operably linked to a vector;

transfecting the construct into a host cell; and harvesting and isolating the protein expressed by the construct in the host cell.

8. The method of claim 7, wherein the host cell is a bacterial cell.

9. The method of claim 7, wherein the host cell is a plant cell.

10. The method of claim 9, wherein the plant cell is a monocot or a dicot.

11. The method of claim 7, wherein the construct is in a plant seed.

12. The method of claim 7, wherein the vector is a binary vector.

13. The method of claim 12, wherein the vector is a pB121 vector.

14. The method of claim 7, wherein the vector is a pET vector.

15. The isolated nucleic acid of claim 1, wherein the isolated nucleic acid encodes a protein isolated from Yuzhu, and wherein the protein inhibits proliferation of cancer cells or viruses.

16. The isolated nucleic acid of claim 15, wherein said cancer cells are MCF-7 or HL-60 cells.

17. The isolated nucleic acid of claim 15, wherein said virus is Herpes simplex virus, a respiratory syncytial virus, Influenza-A virus or avian flu virus (H5N1).

18. The isolated nucleic acid of claim 15, wherein the protein is a homodimer of two subunits and has a molecular weight of 28 kDa.

19. The isolated nucleic acid of claim 15, wherein the protein has a retention time of 29.02±0.74 min in Superdex 75 HR 10/30 column.

* * * * *